United States Patent [19]

Pittet et al.

[11] 4,418,087
[45] Nov. 29, 1983

[54] MIXTURE OF 4,4A,5,6-TETRAHYDRO-7-METHYL-2-(3H)-NAPHTHALENONE AND BENZODIOXANONES AND USE THEREOF IN AUGMENTING OR ENHANCING THE AROMA OR TASTE OF CONSUMABLE MATERIALS

[75] Inventors: Alan O. Pittet, Atlantic Highlands; Ranya Muralidhara, Fair Haven; Myrna L. Hagedorn, Edison, all of N.J.

[73] Assignee: International Flavors & Fragrances Inc., New York, N.Y.

[21] Appl. No.: 482,762

[22] Filed: Apr. 7, 1983

Related U.S. Application Data

[60] Division of Ser. No. 368,640, Apr. 15, 1982, which is a continuation-in-part of Ser. No. 354,111, Mar. 2, 1982, abandoned.

[51] Int. Cl.³ .................. A23L 1/226; A61K 7/46
[52] U.S. Cl. ............................. 426/536; 426/538; 252/522 R
[58] Field of Search .................. 426/536, 538; 252/522 R

[56] References Cited

U.S. PATENT DOCUMENTS 4,241,097 12/1980 Sprecker et al. .................. 426/536
4,385,073 5/1983 Pittet et al. ...................... 426/538

Primary Examiner—Joseph M. Golian
Attorney, Agent, or Firm—Arthur L. Liberman

[57] ABSTRACT

Described are mixtures of 4,4A,5,6-tetrahydro-7-methyl-2-(3H)-naphthalenone having the structure:

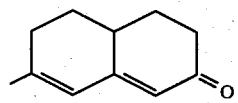

and benzodioxanones having the generic structure:

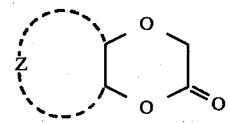

wherein Z is benzo or cyclohexano and uses thereof in augmenting or enhancing the aroma or taste of consumable materials including foodstuffs and fragrances.

2 Claims, 8 Drawing Figures

GLC PROFILE FOR BULKED FRACTIONS 8-13 OF EXAMPLE II.

GLC PROFILE FOR EXAMPLE I. CRUDE

NMR SPECTRUM FOR EXAMPLE II.

GLC PROFILE FOR EXAMPLE III, (CRUDE)

FIG. 5 MASS SPECTRUM FOR EXAMPLE III.

NMR SPECTRUM FOR EXAMPLE III.

IR SPECTRUM FOR EXAMPLE III (CRYSTALS).

GLC PROFILE FOR EXAMPLE Ⅴ.
CRUDE

MIXTURE OF 4,4A,5,6-TETRAHYDRO-7-METHYL-2-(3H)-NAPHTHALENONE AND BENZODIOXANONES AND USE THEREOF IN AUGMENTING OR ENHANCING THE AROMA OR TASTE OF CONSUMABLE MATERIALS

This is a divisional of application Ser. No. 368,640, filed Apr. 15, 1982, which, in turn, is a continuation-in-part of application for U.S. Letters Patent, Ser. No. 354,111 filed on Mar. 2, 1982 now abandoned.

Sweet, lactonic, coconut-like, creamy, coumarin-like, waxy, heliotropin-like, fruity, juicy, rum, sugary and woody nuances are highly desirable in smoking tobacco prior to smoking and sweet, smoothing rich, coumarin-like, creamy, coconut-like, rum-like and caramellic aroma and taste nuances are highly desirable in smoking tobacco on smoking in the main stream and in the side stream.

Coumarinic organoleptic characteristics have heretofore been provided in consumable material by coumarin or homologues or analogues thereof having the structures:

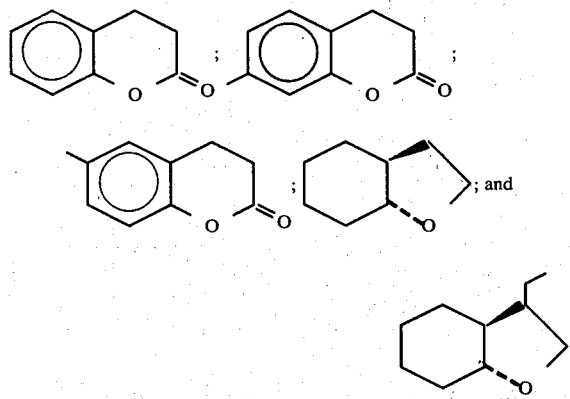

Coumarin, 1,2-benzopyrone having the structure:

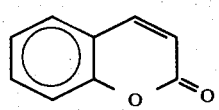

is described in "Perfume and Flavor Chemicals (Aroma Chemicals)" by Stephen Arctander, 1969 (Monograph 704) as being extensively used in perfumery to support herbaceous odors, lavender, lavendin, rosemary, citrus oils, oakmoss, etc. and as a fixative in numerous types of fragrances. Arctander states that coumarin is almost a standard ingredient in Fougere types with amyl salicylate and lavender notes with or without oakmoss. Arctander states that coumarin is not permitted for food use in the United States of America and is also banned from food flavorings in a number of other countries. Arctander further states that the hazardous level of coumarin is estimated at three grams per day for adult human beings. Accordingly, it has been found necessary in the flavor and fragrance industry to find one or a mixture of suitable replacements for coumarin. In U.S. Pat. No. 4,294,266 and in U.S. Pat. No. 4,241,097 bicyclic compounds defined according to the generic structure:

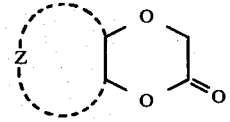

wherein Z is benzo or cyclohexano which generic structure includes the structures:

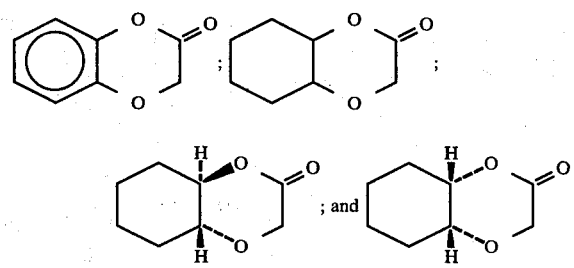

were designed as substitutes for 6-methyl coumarin, 7-methyl coumarin and coumarin itself. However, the compounds having the generic structure:

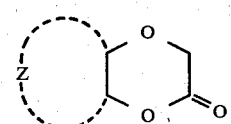

although inexpensive replacements for coumarin, do not have all of the desired coumarin nuances necessary to be a total replacer therefor. Accordingly, a need has arisen for a compound or mixture of compounds which can totally replace coumarin yet which is inexpensive and organoleptically compatible with other flavorants or aromatizing agents in consumable materials.

Tetrahydro naphthalene derivatives are known in the prior art for augmenting or enhancing the aroma or taste of tobaccos. Thus, the compound defined according to the structure:

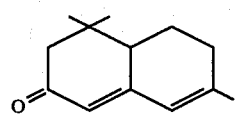

is disclosed in U.K. Patent Specification No. 1,226,730 and in U.S. Pat. No. 3,217,717 as useful for augmenting or enhancing the aroma or taste of smoking tobacco. It is indicated in U.K. Patent Specification No. 1,226,730 (published on Mar. 31, 1971) that the compound defined according to the structure:

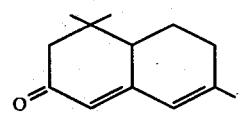

may be produced by reacting the compound having the structure:

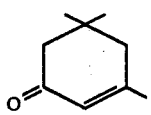

with isopropenyl acetate in order to make a mixture of compounds defined according to the structure:

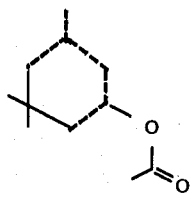

wherein two of the non-adjacent dashed lines in the resulting mixture represent conjugated carbon-carbon double bonds and the other of the dashed lines represent carbon-carbon single bonds; and reacting the resulting mixture defined according to the structure:

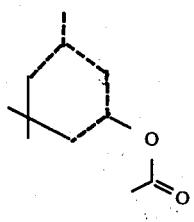

with methyl vinyl ketone according to the reaction:

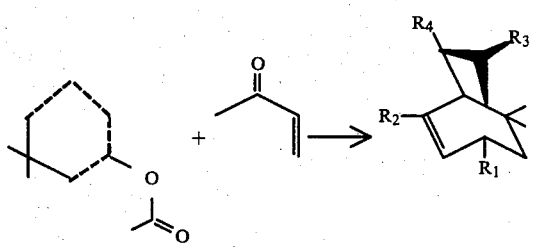

wherein in the resulting mixture defined according to the structure:

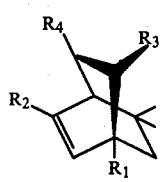

one of $R_3$ or $R_4$ is acetyl and the other of $R_3$ or $R_4$ is hydrogen and one of $R_1$ or $R_2$ is acetoxy and the other of $R_1$ or $R_2$ is methyl; and then rearranging the resulting compounds defined according to the structure:

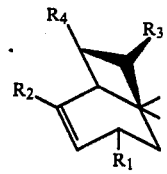

(with the exception of the compound having the structure:

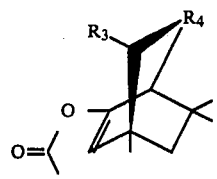

which will not so rearrange), according to the reaction:

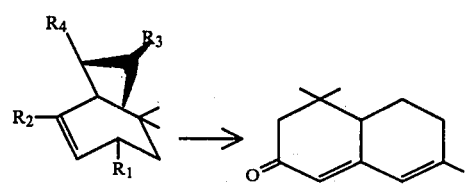

However, the compound defined according to the structure:

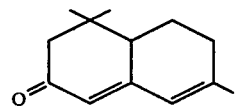

does not have the interesting and important coumarinic-type properties which provide the need that is provided by the material of the instant invention defined according to the structure:

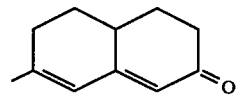

Indeed, the composition of matter of the instant invention, the 4,4A,5,6-tetrahydro-7-methyl-2-(3H)-naphthalenone, has properties which are unexpected and unobvious and advantageous from an organoleptic standpoint.

The prior art has indicated that the compound defined according to the structure:

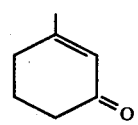

may be prepared by means of a decarboxylation of "Hagemann's Ester" which has the structure:

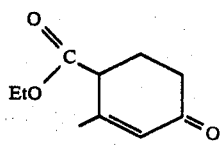

according to the reaction:

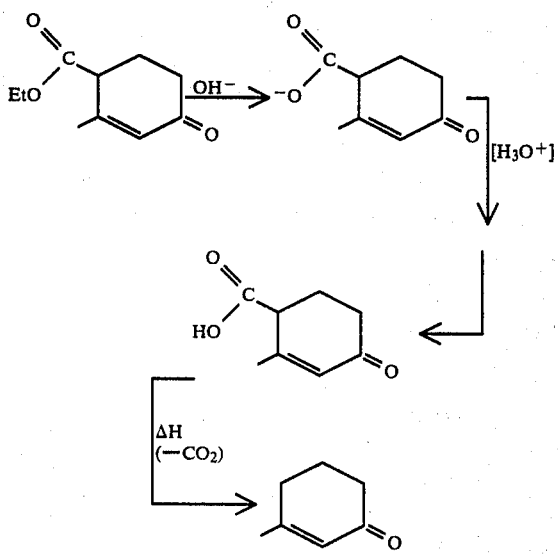

Hagemann's Ester is shown in the prior art to be prepared by reacting two moles of acetoacetic ester with one mole of formaldehyde. Indeed, the compound defined according to the structure:

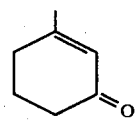

prepared in this manner is shown to be useful in augmenting or enhancing the aroma or taste of foodstuffs, e.g. non-alcoholic beverages, ice creams, candy, baked goods, gelatines, pudding, milk and dairy products in Fenaroli's Handbook of Flavor Ingredients, second edition, volume 2 published by the CRC Press at page 360. Furthermore, Stoll, et al, Helv. Chim. Acta. 30, 2019, 1947 indicates that the compound having the structure:

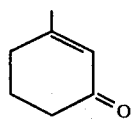

is a natural constituent of *Menth.pulegium* In addition, Fenaroli's Handbook of Flavor Ingredients at page 400 indicates that the compound having the structure:

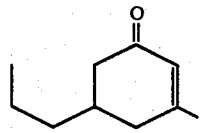

is useful in augmenting or enhancing the aroma or taste of foodstuffs.

In preparing the compound defined according to the structure:

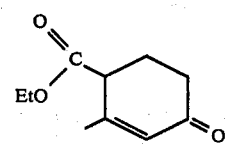

in order to further prepare the compound having the structure:

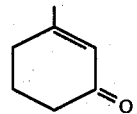

it has been the practice to discard the higher boiling fractions. It is in these higher boiling fractions that the compound having the structure:

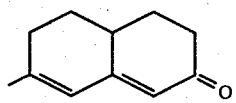

exists. Heretofore, the prior art has failed to disclose and the flavor and fragrance industry has failed to ascertain that the compound defined according to the structure:

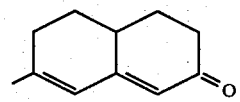

has any utility whatsoever in augmenting or enhancing the aroma or taste of consumable materials.

Indeed, heretofore the prior art has disclosed complicated and uneconomical processes for preparing the compound having the structure:

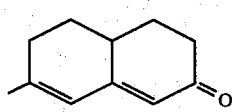

thusly: Prochazka at Chem. Abstracts volume 42:8162h discloses the complicated process:

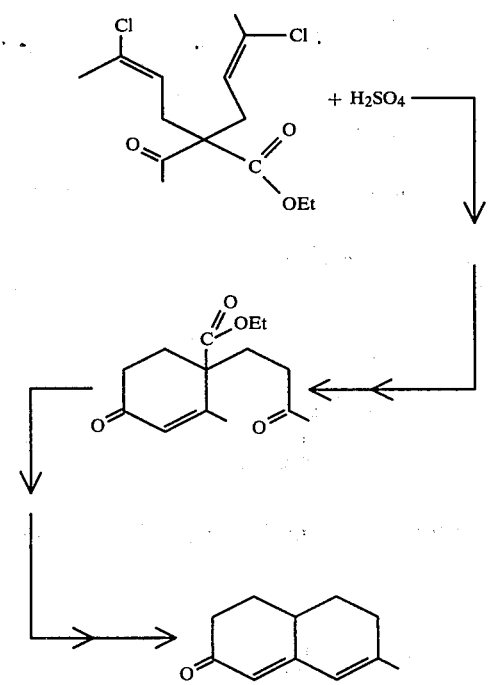

Wilds and Werth, *J. Org. Chem.* 17, 1149(1952) applied a Robinson annelation reaction utilizing a quaterny ammonium derivative to make a tricyclic material from a bicyclic material. Applying this type of reaction, it is possible to form 4,4A,5,6-tetrahydro-7-methyl-2-(3H)-naphthalenone according to the following reaction sequence:

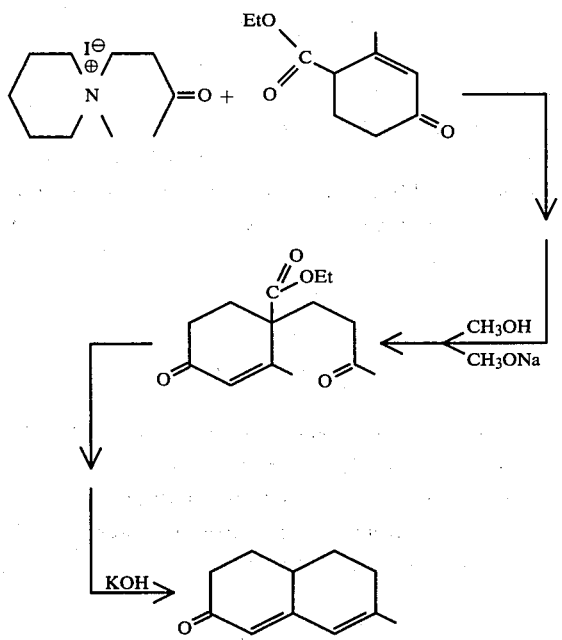

Marshall, et al, Tetrahedron Lett. 1971, (41) 3795-8 disclosed a difficult to perform synthesis of 4,4A,5,6-tetrahydro-7-methyl-2-(3H)-naphthalenone by means of a Birch reduction using liquid ammonia.

Hexahydro naphthalenones are known in nature and are known flavorants in nature as is stated in the publication Tob. Sci. 1972 16, 107–112 (abstracted at Chem. Abstracts Volume 78, 2099y) wherein the compound having the structure:

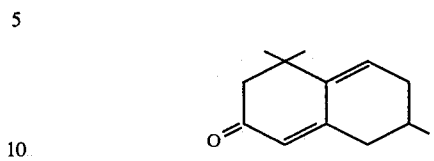

is shown to be present in tobacco flavor. The compound having the structure:

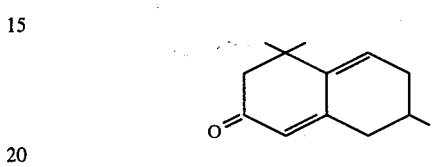

has organoleptic properties different in kind and unexpectedly and unobviously different from the organoleptic properties of the compound having the structure:

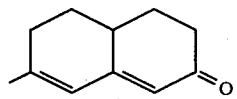

Also, the compound of U.K. Patent Specification No. 1,226,730 having the structure:

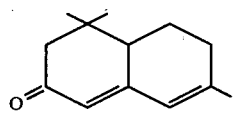

has sweet, woody, herbaceous, fruity notes in the main stream and the side stream on smoking in a smoking tobacco composition. It enhances tobacco character and imparts Virginia-like notes.

From a flavor standpoint, the compound having the structure:

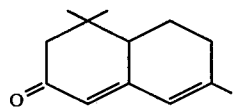

has a dogwood, oak-like, Virginia tobacco-like aroma and taste characteristic at 0.2 ppm. From a perfumery standpoint, the compound having the structure:

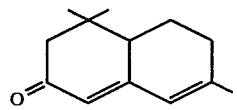

has a powerful tobacco, hay, dried fruit odor and is useful in clover fragrances. However, the compound having the structure:

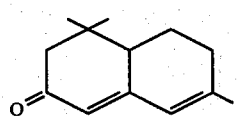

does not have the organoleptic utilities of the compound having the structure:

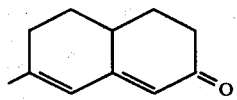

as will be seen from the instant specification.

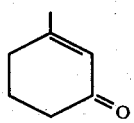

in order to form a mixture of compounds defined according to the structures:

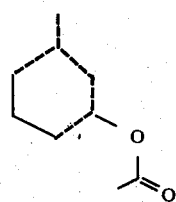

which mixture represents the compounds defined according to the structures:

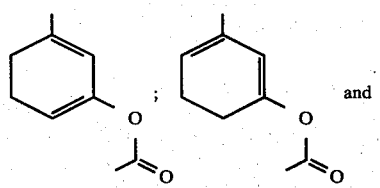

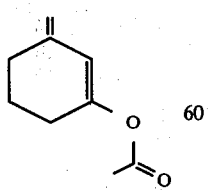

Figure 2:
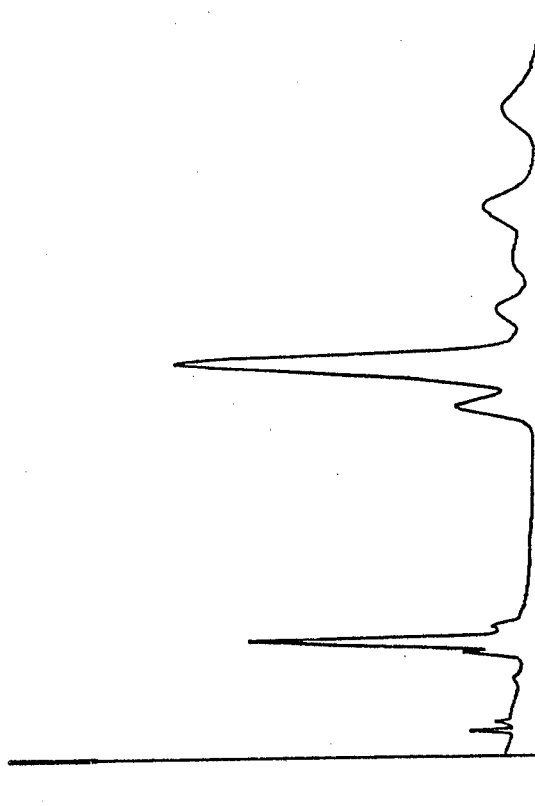

FIG. 2 is the GLC profile for bulked fractions 8–13 of the distillation product of the reaction product of Example II containing the compounds having the structures:

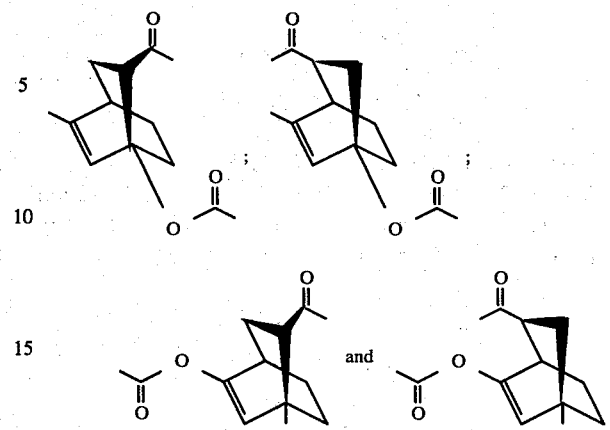

Figure 3:
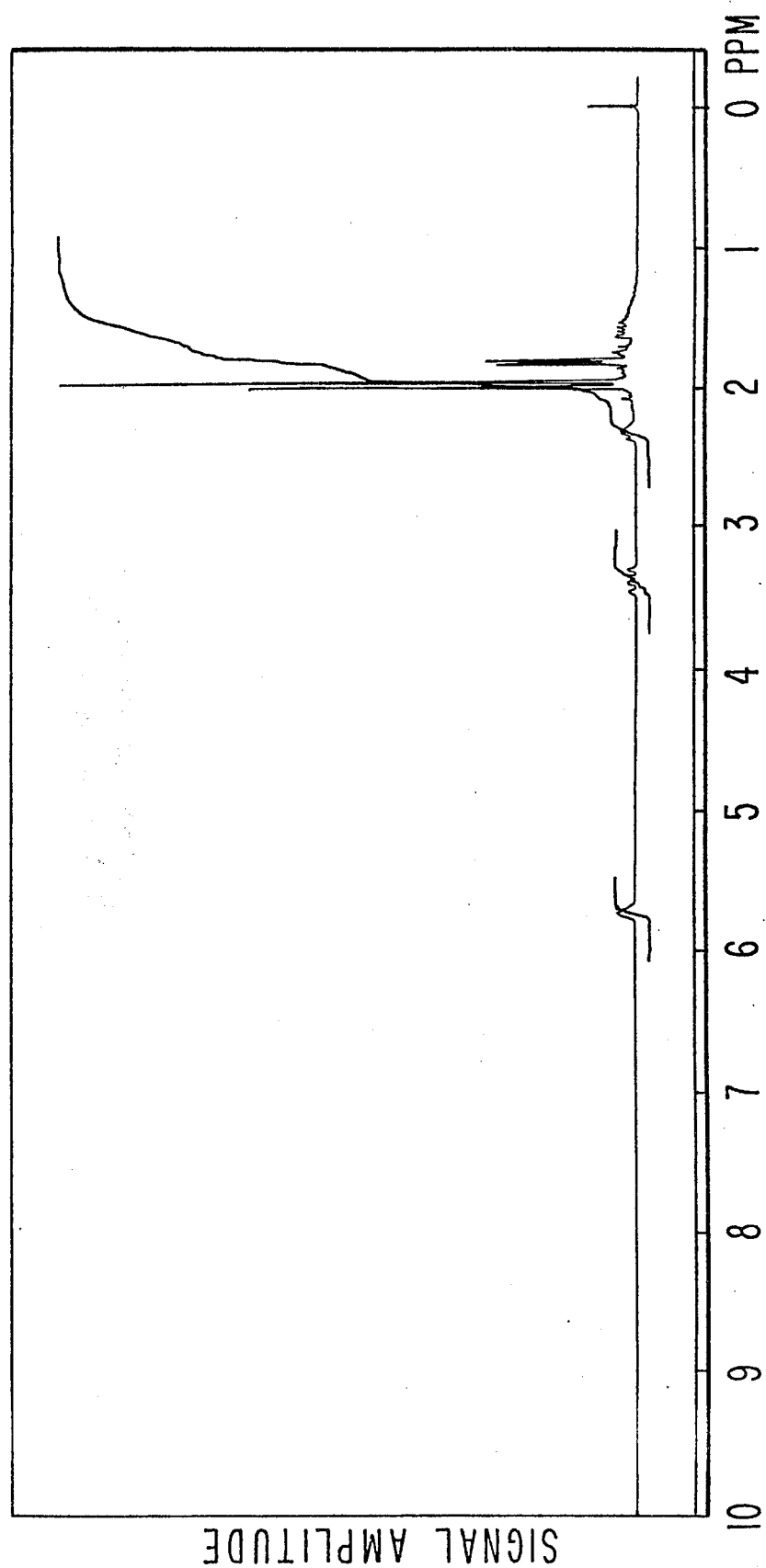

FIG. 3 is the NMR spectrum for the acetate of 5-methyl-7-acetyl-bicyclo[2.2.2]oct-5-en-1-ol produced according to Example II having the structure:

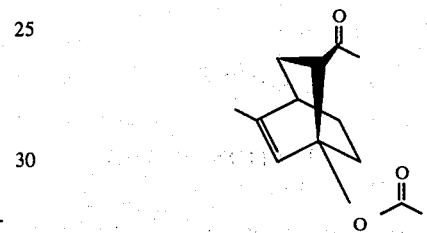

(CFCl$_3$ solvent; Field Strength 100 MHz).

Figure 4:
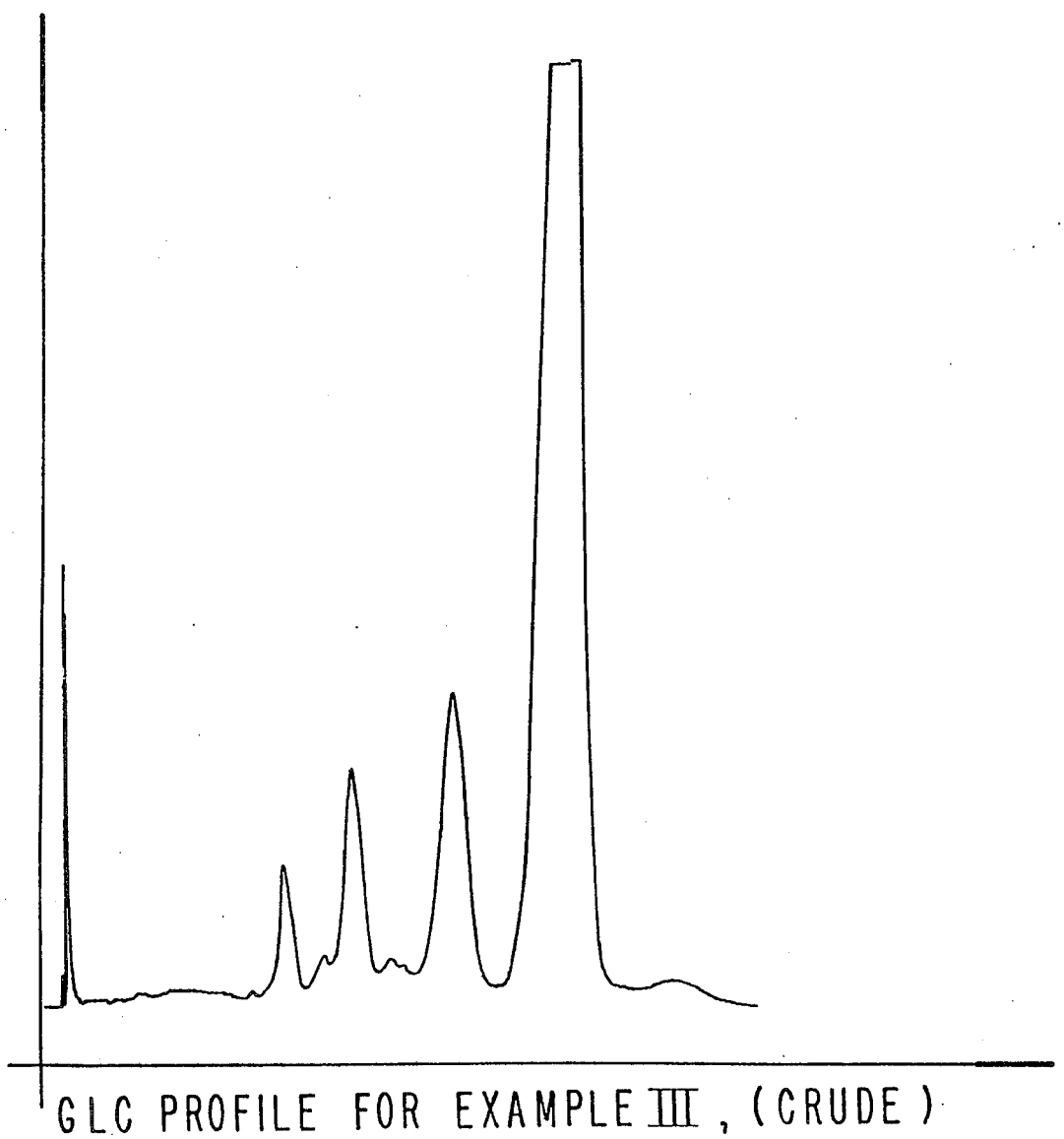

FIG. 4 is the GLC profile for the crude reaction product for Example III containing the compound having the structure:

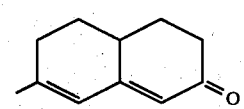

Figure 5:
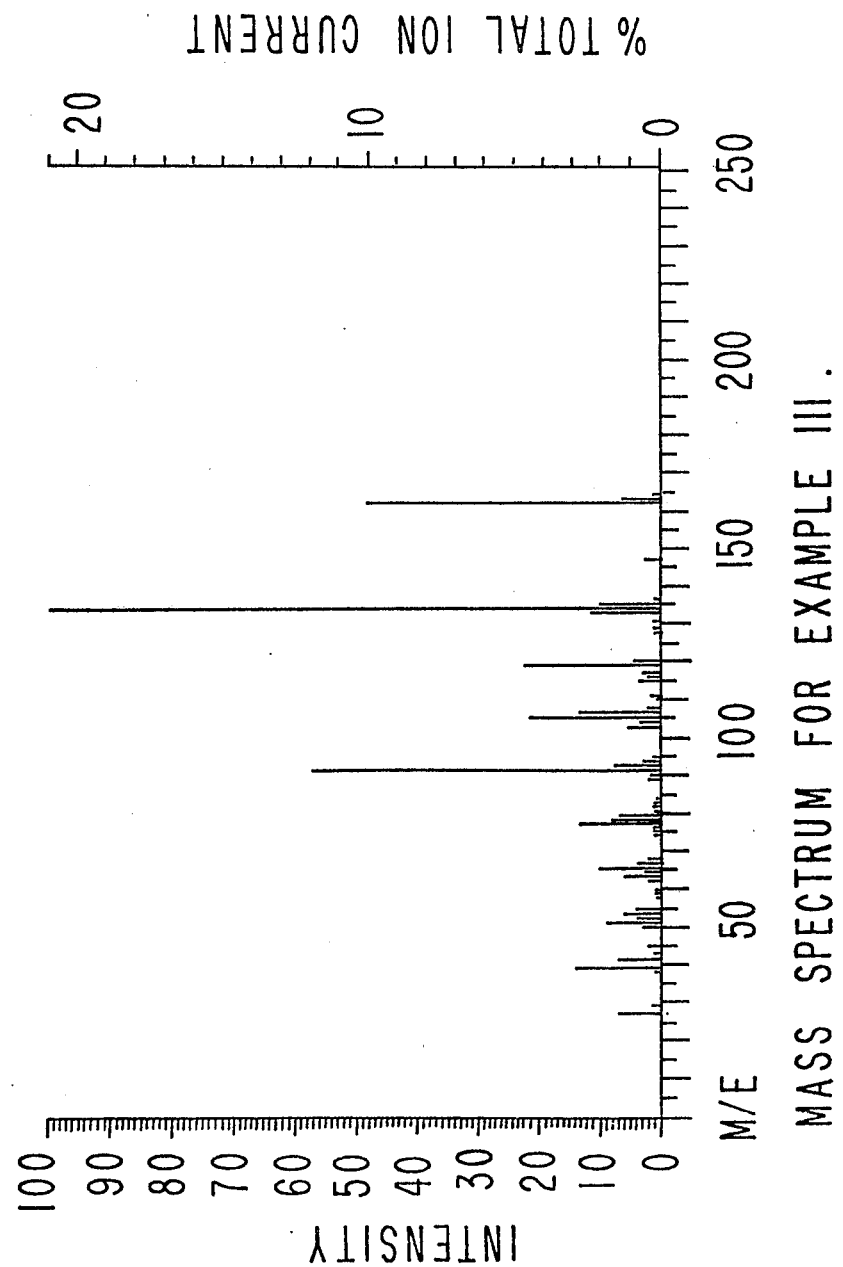

FIG. 5 is the mass spectrum for the compound having the structure:

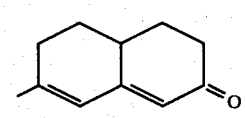

of Example III.

Figure 6:
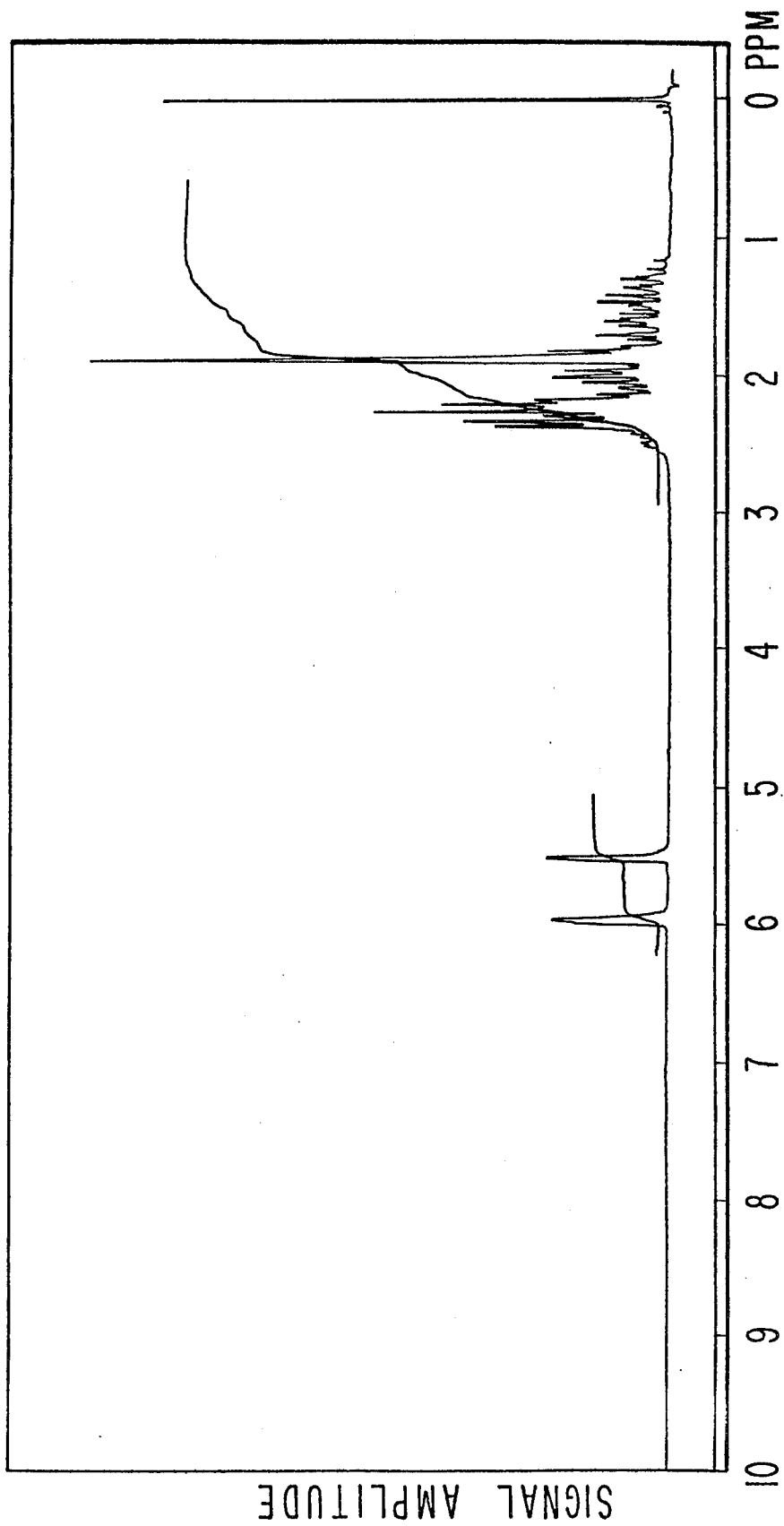

FIG. 6 is the NMR spectrum for the crystalline compound produced according to Example III having the structure:

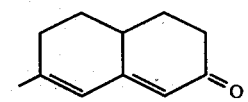

(CFCl$_3$ solvent; Field Strength 100 MHz).

Figure 7:
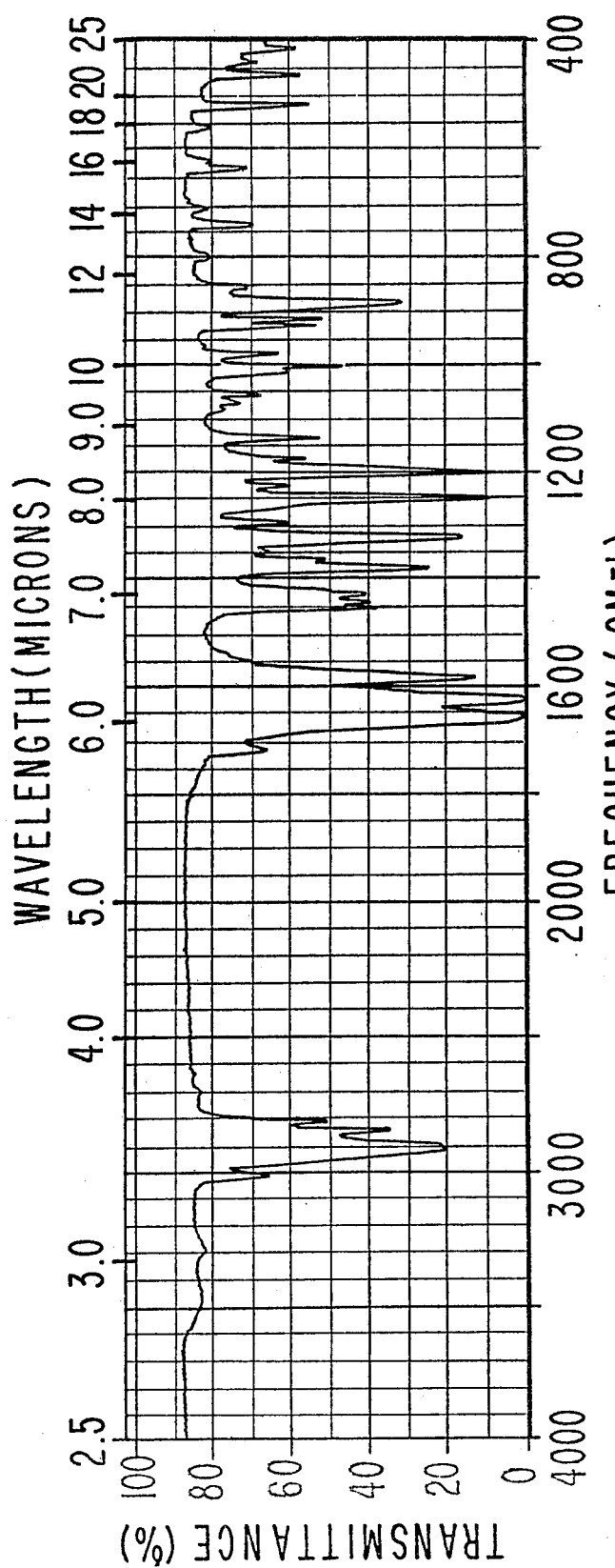

FIG. 7 is the infra-red spectrum for the crystalline compound having the structure:

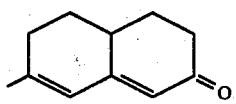

produced according to Example III.

Figure 8:
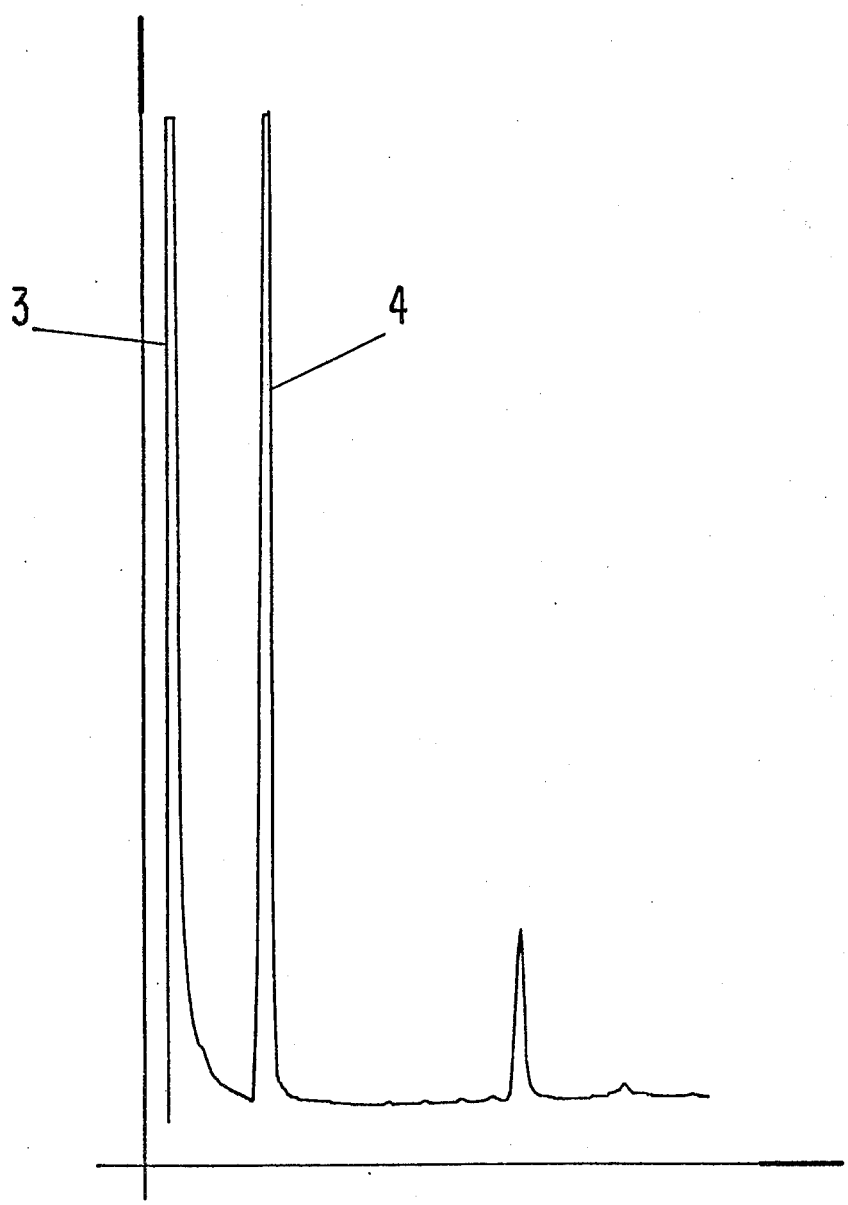

FIG. 8 is the GLC profile for the crude reaction product produced according to Example V containing the compound having the structure:

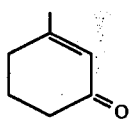

as well as the compound, 4,4A,5,6-tetrahydro-7-methyl-2-(3H)naphthalenene having the structure:

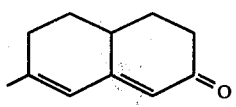

DETAILED DESCRIPTION OF THE DRAWINGS

Figure 1:
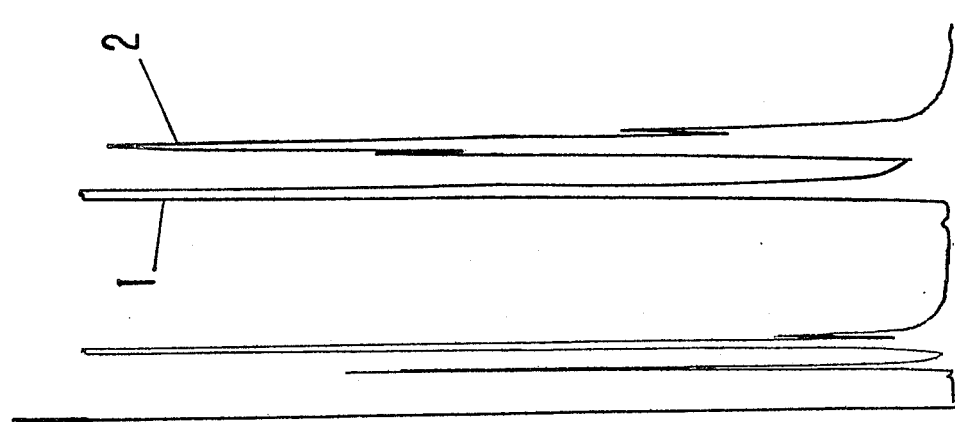
FIG. 1 is the GLC profile for the crude reaction product of Example I resulting from the reaction of isopropenyl acetate with the compound having the structure.

FIG. 1 is the GLC profile for the crude reaction product of Example I containing compounds defined according to the structures:

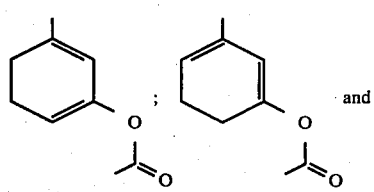

The peak indicated by the reference numeral "1" is the peak for the starting material for the reaction having the structure:

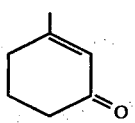

The peak indicated by the reference numeral "2" is a complex peak containing a mixture of the compounds defined according to the structures:

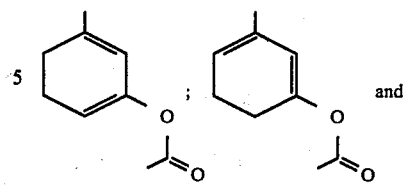

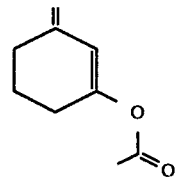

FIG. 8 is the GLC profile for the crude reaction product for production of the compound having the structure:

(conditions: 2'×⅛" Carbowax column programmed at 100°–220° C. at 8° C. per minute). The peak indicated by reference numeral "3" is the peak for the solvent for this reaction. The peak indicated by reference numeral "4" is the peak for the reaction product having the structure:

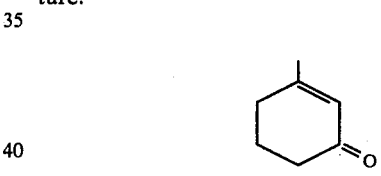

The peak indicated by reference numeral "5" is the peak for the compound having the structure:

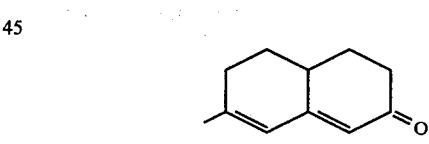

THE INVENTION

It has now been discovered that novel solid and liquid foodstuff, chewing gum, toothpaste, medicinal product, chewing tobacco compositions and flavoring compositions therefor having coumarin-like, coconut, lactonic, hay-like, macaroon-like and sweet aromas and hay-like, coumarin-like, coconut-like, lactonic, almond-like, macaroon-like, sweet and bitter tastes; and novel perfume compositions, perfumed articles (such as solid or liquid anionic, cationic, nonionic or zwitterionic detergents, fabric softener compositions, disposable fabric softener articles, cosmetic powders and perfumed polymers) and colognes having natural and diffusive coumarin-like, tonka-like, fruity, tobacco-like and sweet rum aroma profiles with spicy, hay and tobacco-like topnotes; as well as novel smoking tobaccos and smoking tobacco flavoring compositions having, prior to smoking, sweet, lactonic, coconut-like, coumarin-like, creamy, waxy, heliotropine-like, fruity, juicy, rum, sugary and woody aroma nuances and on smoking in both the main stream and the side stream sweet, smoothing rich, coumarin-like, creamy, coconut-like, rum-like and caramellic aroma and taste nuances may be provided by the utilization of 4,4A,5,6-tetrahydro-7-methyl-2-(3H)-naphthalenone having the structure:

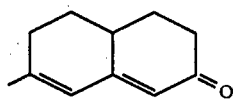

having a purity of 85% or greater. The 4,4A,5,6-tetrahydro-7-methyl-2-(3H)-naphthalenone in the crystalline state of about 100% purity having the structure:

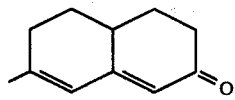

is a novel composition of matter.

The 4,4A,5,6-tetrahydro-7-methyl-2-(3H)-naphthalenone of our invention having the structure:

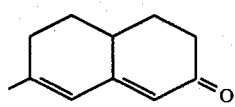

may be produced according to two alternative and novel processes. The first process involves the reaction of two moles of formaldehyde with three moles of acetoacetic ester according to a reaction which may proceed in one of the following postulated fashions:

(A)
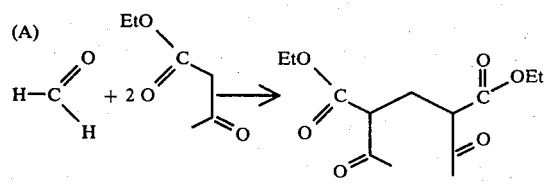

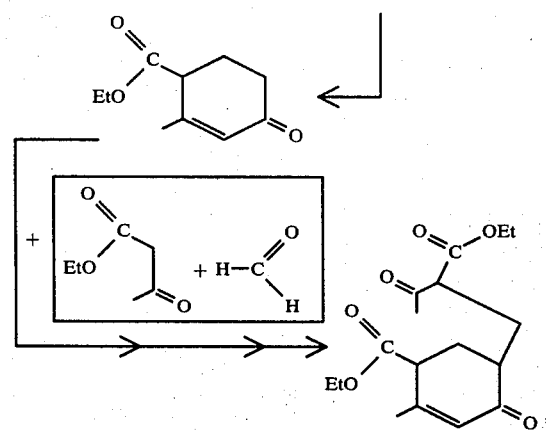

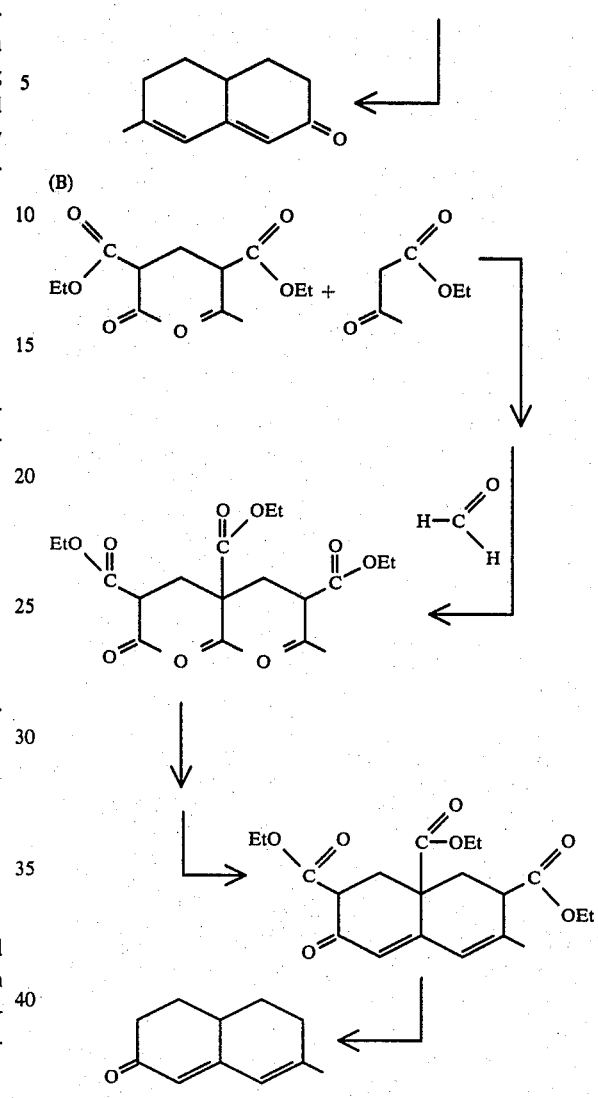

After formation of the polycarboxylic acid ketoester, the diester is then saponified, acidified and finally heated whereby the carboxylic acid moieties are removed by decarboxylation with the evolution of carbon dioxide in order to form the 4,4A,5,6-tetrahydro-7-methyl-2-(3H)-naphthalenone having the structure:

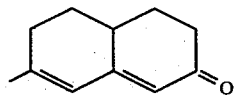

In this reaction, the mole ratio of acetoacetic ester:formaldehyde is 3:2. The length of time required for the reaction to proceed must be such that the additional formaldehyde and acetoacetic ester react with the preformed acetoacetic ester-formaldehyde adduct (probably the "Hagemann's ester"). The reaction to form the polycarboxylate preferably takes place in the presence of a base such as piperadine. The formaldehyde may be formaldehyde itself or a formaldehyde source such as paraformaldehyde or formalin (40% aqueous formaldehyde). The reaction temperature varies between 95° C.

and 110° C. and the reaction time varies between one hour and four hours. Reaction time of less than one hour and reaction temperatures of less than 95° C. will not give rise to economical yields of the polycarboxylic acid ester intermediate but instead give rise to high yields of the undesired Hagemann's ester. At the completion of the formation of the polycarboxylic acid ester, the reaction product is decarboxylated using a decarboxylation procedure which is the acidification of the reaction mass using such concentrated protonic acid as concentrated sulfuric acid, para toluenesulfonic acid or mixtures of same. The decarboxylation time is preferably about five hours and the decarboxylation temperature is preferably between 85° C. and 105° C. at pressures of about atmospheric pressure. The equivalent ratio of polycarboxylic acid ester:protonic acid should be about 1:1. If any reagent is used in excess, it is the protonic acid. Thus, for example, when using sulfuric acid as a decarboxylation reagent, the weight ratio of sulfuric acid (concentrated): polycarboxylic acid ester varies betweeen about 3:4 up to about 4:3.

At the end of the reaction, the reaction product is fractionally distilled and the fraction distilling at a vapor temperature of 96° C. and a liquid temperature of 156° C.; and a vacuum of 3 mm/Hg pressure is approximately 85–90% 4,4A,5,6-tetrahydro-7-methyl-2-(3H)-naphthalenone having the structure:

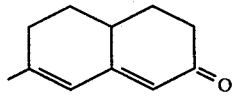

The compound having the structure:

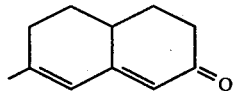

may also be economically prepared by decarboxylating the Hagemann's ester formed from the reaction of one mole of formaldehyde and two moles of acetoacetic ester whereby the compound having the structure:

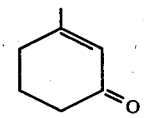

is formed. This compound is then reacted with isopropenyl acetate to form a mixture of compounds defined according to the structure:

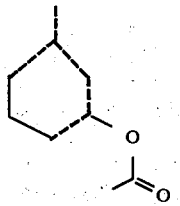

wherein two of the dashed lines not adjacent to one another represent conjugated carbon-carbon double bonds and the other of the dashed lines represent carbon-carbon single bonds. The compounds have the structures:

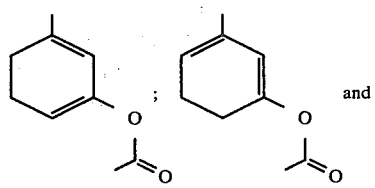

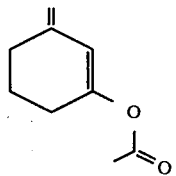

This mixture is then conveniently reacted via a Diels-Alder reaction at higher temperatures or using a Lewis acid catalyst such as stannic chloride or zinc chloride or boron-trifluoride etherate with methyl vinyl ketone having the structure:

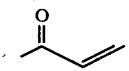

thereby forming a mixture of compounds defined according to the structure:

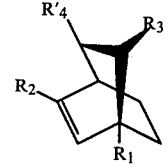

wherein in the mixture, one of $R_3$ or $R_4$ is hydrogen and the other of $R_3$ or $R_4$ is acetyl and one of $R_1$ or $R_2$ is methyl and the other of $R_1$ or $R_2$ is acetoxy, to wit compounds having the structures:

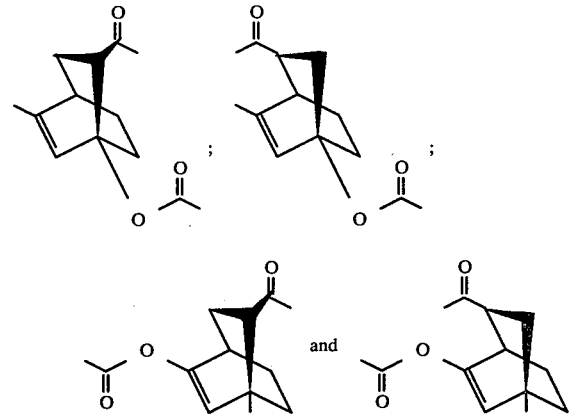

It has been postulated that the compound having the structure:

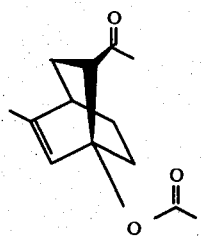

can be rearranged by heating with base or solutions of base to form the compound having the structure:

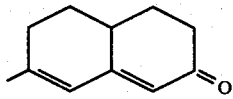

However, the reaction may be best shown as a rearrangement thusly:

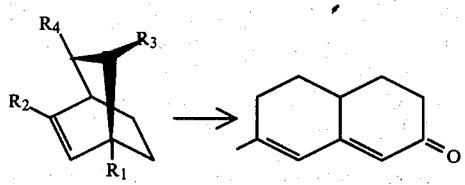

In general, the sequence of reactions described above is as follows:

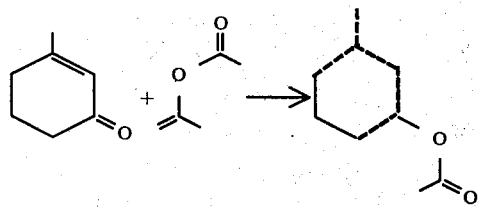   I.

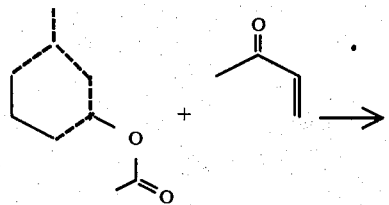   II.

and

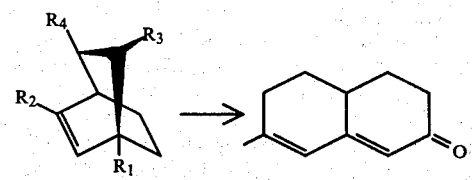   III.

The reaction of the ketone having the structure:

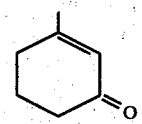

with the isopropenyl acetate having the structure:

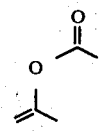

to form the mixture of compounds defined according to the structure:

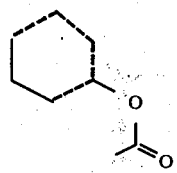

preferably takes place in the presence of a protonic acid catalyst such as paratoluene sulfonic acid, sulfuric acid or phosphoric acid. The mole ratio of 3-methylcyclohexenone: isopropenyl acetate may vary from about 0.5:1 up to about 1.5:1 with a preferred mole ratio of 1:1. The concentration of protonic acid in the reaction mass may vary from about 0.01% up to about 0.5%. The reaction temperature may vary from about 100° C. up to about 150° C. at from atmospheric pressure up to about 5 atmospheres. During the reaction, the water of reaction is continuously removed. At the end of the reaction, the reaction product is distilled yielding the mixture of compounds defined according to the structure:

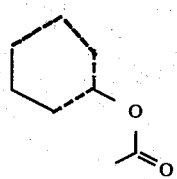

The resulting mixture is further reacted with methyl vinyl ketone according to the reaction:

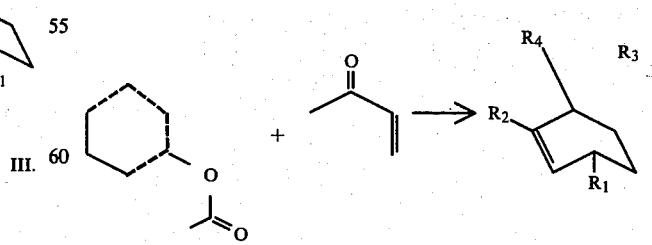

This reaction, a Diels-Alder reaction, may take place without a catalyst (e.g. a Lewis acid catalyst) at higher temperatures, e.g. reflux temperatures, e.g. from 110° up to 150° C. at pressures of atmospheric up to about 5 atmospheres or the reaction may take place at lower temperatures, e.g. 70° C. using a Lewis acid catalyst such as stannic chloride, borontrifluoride etherate or zinc chloride. When using no catalyst at higher temperatures, the Diels-Alder reaction takes place preferably at reflux conditions over a period of between four hours and eight hours. At the end of the reaction, the resulting reaction mixture is distilled yielding a mixture of compounds defined according to the structures:

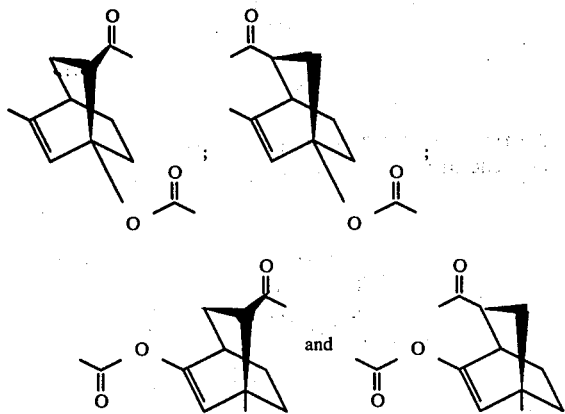

The resulting mixture of compounds is then subjected to a rearrangement reaction shown mostly:

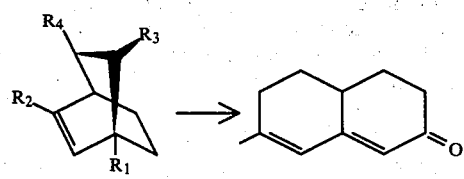

which takes place in the presence of a strong base such as sodium hydroxide, potassium hydroxide or lithium hydroxide. The rearrangement reaction is carried out in the presence of an inert solvent such as methanol, isopropanol or ethanol which solvent will permit conventional refluxing at a temperature such that the time of reaction will vary between about one hour and about three hours. Too low a boiling solvent will necessitate a pressure substantially higher than atmospheric pressure thereby giving rise to the requirement of more expensive complicated apparatus or such a long time of reaction as to render the cost of carrying out the reaction prohibitively high.

At the end of the reaction, the reaction product is distilled and if desired, the distillation fractions containing 99% or more of 4,4A,5,6-tetrahydro-7-methyl-2-(3H)-naphthalenone having the structure:

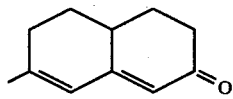

are crystallized thereby yielding a highly pure form of 4,4A,5,6-tetrahydro-7-methyl-2-(3H)-naphthalenone which form is novel.

The compound of our invention; 4,4A,5,6-tetrahydro-7-methyl-2-(3H)-naphthalenone, having the structure:

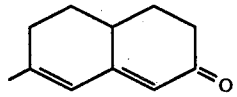

is capable of supplying and/or potentiating certain flavor and aroma notes usually lacking in many fruit flavors as well as tobacco flavors heretofore. Furthermore, the 4,4A,5,6-tetrahydro-7-methyl-2-(3H)-naphthalenone of our invention is capable of supplying certain fragrance notes usually lacking in many perfumery materials, for example, Fougère formulations, lavendin formulations, citrusy formulations and oakmoss-type formulations. In addition, this material is capable of acting as a fixative in perfumery while augmenting or enhancing certain aroma nuances in itself.

As used herein, the term "foodstuff" includes both solid and liquid ingestible materials which usually do, but need not, have nutritional value. Thus, foodstuffs includes soups, convenience foods, beverages, dairy products, candies, vegetable cereals, soft drinks, snacks and the like.

As used herein, the term "medicinal products" includes both solids and liquids which are ingestible non-toxic materials which have medicinal value such as cough syrups, cough drops and chewable medicinal tablets.

The term "chewing gum" is intended herein to be a foodstuff composition comprising a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g. glycerine and a flavoring composition which incorporates one or more of the 4,4A,5,6-tetrahydro-7-methyl-2-(3H)-naphthalenones of our invention, and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable" and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthetically pleasing aroma and taste profile. Such material, in general, may be characterized as flavoring adjuvants or vehicles comprising broadly, stabilizers, thickeners, surface active agents, conditioners, other flavorants and flavor intensifiers.

Stabilizer compounds include preservatives, e.g. sodium chloride; antioxidants, e.g. calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan, cellulose and cellulose derivatives such as carboxymethyl cellulose and methyl cellulose; natural and synthetic gums such as gum arabic, gum tragacanth, gelatin, proteinaceous materials; lipids; carbohydrates; starches, pectins and emulsifiers, e.g. mono- and diglycerides of fatty acids, skim milk powder, hexoses, pentoses, disaccharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like, colorants, e.g. carminic acid, cochineal, tumeric and curcumin and the like, firming agents such as aluminum sodium sulfate, calcium chloride and calcium glyconate, texturizers, anti-caking agents, e.g. aluminum calcium sulfate and tribasic calcium phosphate, enzymes, yeast foods, e.g. calcium lactate and calcium sulfate, nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-cis-3-pentenoic acid; ketones and aldehydes, e.g. acetaldehyde, acetophenone, acetone, acetyl methyl carbinol, acrolein, n-butanal, crotonal, diacetyl, beta,beta-dimethyl-acrolein, n-hexanal, 2-hexanal, cis-3-hexenal, 2-heptenal, 4-(p-hydroxyphenyl)-2-butanone, alpha-ionone, beta-ionone, 2-methyl-3-butanone, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1,cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate, esters, such as butyl acetate, ethyl acetate, ethyl acetoacetate; ethyl benzoate, ethyl butyrate, ethyl caproate, ethyl cinnamate, ethyl crotonate, ethyl formate, ethyl isobutyrate, ethyl isovalerate, ethyl alpha-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methyl-butyrate, propyl acetate, amyl acetate, amyl butyrate, benzyl salicylate, dimethyl anthranilate, ethyl methylphenyl-glycidate ethyl succinate isobutyl cinnamate and terpenyl acetate; essential oils such as jasmin absolute, rose absolute, orris absolute, lemon essential oil, Bulgarian rose, yara yara, natural raspberry oil and vanilla; lactones, sulfides, e.g. methyl sulfide and other materials such as maltol, acetoin and acetals (e.g. 1,1-diethoxyethane,1,1-dimethoxyethane and dimethoxymethane.

The specific flavoring adjuvant selected for use may be either solid or liquid depending upon the desired physical form of the ultimate product, i.e. foodstuff, whether simulated or natural, and should, in any event, be capable of providing an environment in which the cyclic chemical compounds can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g. simulated foodstuffs, ingredients capable of providing normally solid compositions should be selected such as various cellulose derivatives.

As will be appreciated by those skilled in the art, the amount of 4,4A,5,6-tetrahydro-7-methyl-2-(3H)-naphthalenone employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected (to be effective) be sufficient to augment or enhance the organoleptic characteristics of the parent composition (whether foodstuff per se or flavoring composition).

The use of insufficient quantities of 4,4A,5,6-tetrahydro-7-methyl-2-(3H)-naphthalenone will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of 4,4A,5,6-tetrahydro-7-methyl-2-(3H)-naphthalenone ranging from a small but effective amount, e.g. 0.1 parts per million up to about 20 parts per million by weight based on total composition are suitable. Concentrations in excess of the maximum quantity stated are not normally recommended, since they fail to provide commensurate enhancement of organoleptic properties. In those instances, wherein the 4,4A,5,6-tetrahydro-7-methyl-2-(3H)-naphthalenone is added to the foodstuff as an integral component of a flavoring composition, it is, of course, essential that the total quantity of flavoring composition employed by sufficient to yield an effective 4,4A,5,6-tetrahydro-7-methyl-2-(3H)-naphthalenone concentration in the foodstuff product.

Food flavoring compositions prepared in accordance with the present invention preferably contain the 4,4A,5,6-tetrahydro-7-methyl-2-(3H)-naphthalenone in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 4,4A,5,6-tetrahydro-7-methyl-2-(3H)-naphthalenone of our invention with, for example, gum arabic, gum tragacanth, carrageenan and the like, and thereafter spray-drying the resultant mixture whereby to obtain the particulate solid product. Preprepared flavor mixes in powder form, e.g. a fruit flavored powdered mix, are obtained by mixing the dried solid components, e.g. starch, sugar and the like and 4,4A,5,6-tetrahydro-7-methyl-2-(3H)-naphthalenone in a dry blender until the requisite degree of uniformity is achieved.

It is presently preferred to combine with the 4,4A,5,6-tetrahydro-7-methyl-2-(3H)-naphthalenone the following adjuvants:
p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
1-(3-(methylthio)butyryl-2,6,6-trimethyl cyclohexene;
1(3(methylthio)butyryl)-2,6,6-trimethyl-1,3-cyclohexadiene;
Naphthyl ethyl ether;
Diacetyl;
Ethyl acetate;
Anethole;
Isoamyl butyrate;
Cis-3-hexenol-1;
2-Methyl-2-pentenoic acid;
2-Methyl-cis-3-pentenoic acid;
Ethyl-2-methyl-cis-3-pentenoate;
Methyl-2-methyl-cis-3-pentenoate;
Elemecine (4-allyl-1,2,6-trimethoxy benzene);
Isoelemacine (4-propenyl-1,2,6-trimethoxy benzene); and
2-(4-hydroxy-4-methylpentyl)norbornadiene prepared according to U.S. Pat. No. 3,886,289, issued on May 27, 1975.

An additional aspect of our invention provides an organoleptically improved smoking tobacco product and additives therefor as well as methods of making the same which overcome specific problems heretofore encountered in which specific desired sweet, creamy, coumarin-like, smoothing rich, fruity, rum, sugary and woody flavor and aroma characteristics are created or enhanced and may be readily controlled and maintained at the desired uniform level regardless of variations in the tobacco components of the blend.

This invention further provides improved tobacco aditives and methods whereby various desirable sweet, lactonic, coconut-like, creamy, coumarin-like, waxy, heliotropin-like, fruity, juicy, rum-like, sugary and woody aroma characteristics may be imparted to smoking tobacco products prior to smoking and sweet, smoothing rich, coumarin-like, creamy, coconut-like, rum-like and caramellic aroma and taste characteristics may be readily imparted to smoking tobacco products on smoking in the main stream and in the side stream and may be readily varied and controlled to produce the desired uniform flavoring and aroma characteristics.

In carrying out this aspect of our invention, we add to smoking tobacco materials or a suitable substitute therefor (e.g. dried lettuce leaves) an aroma and flavor additive containing as an active ingredient 4,4A,5,6-tetrahydro-7-methyl-2-(3H)-naphthalenone having the structure:

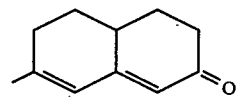

In addition to the 4,4A,5,6-tetrahydro-7-methyl-2-(3H)-naphthalenone of our invention, other flavoring and aroma additives may be added to the smoking tobacco material or substitute therefor either separately or in admixture with the 4,4A,5,6-tetrahydro-7-methyl-2-(3H)-naphthalenone of our invention as follows:

I. Synthetic Materials

Beta-ethyl-cinnamaldehyde;
Eugenol;
Dipentene;
β-Damascone;
β-Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;

Dodecahydro-3a,6,6,9a-tetramethyl naphtho-(2,1,-b-)-furan;
4-Hydroxy hexanoic acid, gamma lactone;
Polyisoprenoid hydrocarbons defined in Example V of U.S. Pat. No. 3,589,372, issued on June 29, 1971.

II. Natural Oils

Celery seed oil;
Coffee extract;
Bergamot Oil;
Cocoa extract;
Nutmeg oil; and
Origanum oil;

An aroma and flavoring concentrate containing the 4,4A,5,6-tetrahydro-7-methyl-2-(3H)-naphthalenone of our invention and if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g. lettuce leaves) or mixtures thereof. The proportions of flavoring additives may be varied in accordance with taste but insofar as the augmentation or the enhancement or the imparting of the sweet, lactonic, coconut-like, creamy, coumarin-like, waxy, heliotropin-like, fruity, juicy, rum, sugary and woody aroma notes are concerned and insofar as the sweet, smoothing rich, coumarin-like, creamy, coconut-like, rum-like and caramellic aroma notes on smoking are concerned, we have found that satisfactory results are obtained if the proportion by weight of the 4,4A,5,6-tetrahydro-7-methyl-2-(3H)-naphthalenone to smoking tobacco material is between 100 ppm and 1,500 ppm (0.025%–0.15%) of the 4,4A,5,6-tetrahydro-7-methyl-2-(3H)-naphthalenone to the smoking tobacco material. We have found further that satisfactory results are obtained if the proportion by weight of the 4,4A,5,6-tetrahydro-7-methyl-2-(3H)-naphthalenone used to flavoring material is between 1,000 and 10,000 ppm (0.1–1.0%).

Any convenient method for incorporating the 4,4A,5,6-tetrahydro-7-methyl-2-(3H)-naphthalenone of our invention may be employed. Thus the 4,4A,5,6-tetrahydro-7-methyl-2-(3H)-naphthalenone taken alone or along with other flavoring additives may be dissolved in a suitable solvent such as ethanol, n-pentane, diethyl ether and/or other volatile organic solvents and the resulting solution may either by sprayed on the cured, cased and blended tobacco material or the tobacco material may be dipped into such solution. Under certain circumstances, a solution of 4,4A,5,6-tetrahydro-7-methyl-2-(3H)-naphthalenone taken alone or further together with other flavoring additives as set forth above, may be applied by means of a suitable applicator such as a brush or roller on the paper or leaf wrapper for the smoking product or it may be applied to the filter by either spraying, dipping or coating.

Furthermore, it will be apparent that only a portion of the tobacco or substitute therefor need be treated and the thus treated tobacco may be blended with other tobaccos before the ultimate tobacco product is formed. In such cases the tobacco treated may have the 4,4A,5,6-tetrahydro-7-methyl-2-(3H)-naphthalenone in excess of the amounts or concentrations above indicated, so that when blended with other tobaccos, the final product will have the percentage within the indicated range.

In accordance with one specific example of our invention, an aged, cured and shredded domestic burley tobacco is spread with a 20% ethyl alcohol solution of 4,4A,5,6-tetrahydro-7-methyl-2-(3H)-naphthalenone to provide a tobacco composition containing 800 ppm by weight of 4,4A,5,6-tetrahydro-7-methyl-2-(3H)-naphthalenone on a dry basis. Thereafter the alcohol is removed by evaporation and the tobacco is manufactured into cigarettes by the usual techniques. The cigarette, when treated as indicated, has a desired and pleasing aroma which is detectable in the main and side streams when the cigarette is smoked. This aroma is described as being sweet, smoothing rich, coumarin-like, creamy, coconut-like, rum-like and caramellic.

While our invention is particularly useful in the manufacture of smoking tobacco, such as cigarette tobacco, cigar tobacco and pipe tobacco, other tobacco products formed from sheeted tobacco dust or fines may also be used. Likewise the 4,4A,5,6-tetrahydro-7-methyl-2-(3H)-naphthalenone of our invention can be incorporated with material such as filter tip materials, seam paste, packaging materials and the like which are used along with tobacco to form a product adapted for smoking. Furthermore, the 4,4A,5,6-tetrahydro-7-methyl-2-(3H)-naphthalenone of our invention can be added to certain tobacco substitutes of natural or synthetic origin (e.g. dried lettuce leaves) and, accordingly, by the term "tobacco" as used throughout this specification, is meant any composition intended for human consumption by smoking or otherwise, whether composed of tobacco plant parts or substitute materials or both.

The 4,4A,5,6-tetrahydro-7-methyl-2-(3H)-naphthalenone having the structure:

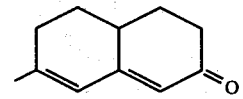

of our invention either in 85% form (as produced according to Example IV infra) or in 100% crystalline form (as produced according to Example III infra) or any range there between and one or more auxilliary perfume ingredients including, for example, alcohols, aldehydes, nitriles, esters, ketones other than the 4,4A,5,6-tetrahydro-7-methyl-2-(3H)-naphthalenone of our invention, cyclic esters, synthetic essential oils, ethers and natural essential oils may be admixed so that the combined odor of the individual components produces a pleasant and desired fragrance particularly and preferably insofar as floral fragrances are concerned.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual components which contribute particular olfactory characteristics but the overall effect of the perfume composition will be the sum of the effects of each of the ingredients. Thus, the 4,4A,5,6-tetrahydro-7-methyl-2-(3H)-naphthalenone of our invention having the structure:

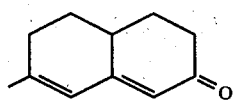

can be used to alter the aroma characteristics of a perfume composition, for example, by utilizing or moderating the olfactory reaction contributed by another ingredient in the composition.

The amount of 4,4,A,5,6-tetrahydro-7-methyl-2-(3H)-naphthalenone of our invention which will be effective in perfume compositions depends on many factors, including the other ingredients, their amounts and the effects which are desired. It has been found that perfume compositions containing as little as 0.05% of the 4,4A,5,6-tetrahydro-7-methyl-2-(3H)-naphthalenone and even less (e.g. 0.02%) can be used to impart natural and diffusive coumarin-like, tonka-like, fruity, tobacco-like, sweet and sweet rum aroma nuances with spicy, hay and tobacco-like topnotes to soaps, cosmetics or other products. The amount employed can range up to 10% of the fragrance components and will depend on considerations of cost, nature of the end product, the effect desired on the finished product and the particular fragrance sought.

The 4,4A,5,6-tetrahydro-7-methyl-2-(3H)-naphthalenone of our invention is useful taken alone or in perfume compositions as an olfactory component in detergents and soaps, space odorants and deodorants, perfumes per se, colognes per se, toilet water, bath preparations such as bath oils and bath solids; hair preparations such as lacquers, brilliantines, pomades and shampoos; cosmetic preparations such as creams, deodorants, hand lotions and sun screens; powders such as talc, dusting powders, face powders and the like. When used as an olfactory component, as little as 0.01% of the 4,4A,5,6-tetrahydro-7-methyl-2-(3H)-naphthalenone of our invention will suffice to impart a natural and diffusive coumarin-like, tonka-like, fruity, tobacco-like, and sweet rum aroma profile to perfumed articles. Generally no more than 3% of the 4,4A,5,6-tetrahydro-7-methyl-2-(3H)-naphthalenone of our invention based on the ultimate end product is required in the perfumed article.

Thus insofar as perfumed articles are concerned, the amount of 4,4A,5,6-tetrahydro-7-methyl-2-(3H)-naphthalenone of our invention having the structure:

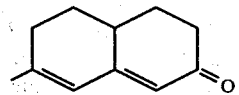

can vary from 0.01% by weight up to 3.0% by weight based on the total weight of the perfumed article, that is, based on the total weight of such materials as anionic, cationic, nonionic or zwitterionic solid or liquid detergent bases; or fabric softener compositions, or fabric softener articles, or perfumed polymers.

In addition, the perfume composition or fragrance composition of our invention can contain a vehicle or carrier for the 4,4A,5,6-tetrahydro-7-methyl-2-(3H)-naphthalenone of our invention. The vehicle can be a liquid such as a non-toxic alcohol, a non-toxic glycol or the like. The carrier can be an absorbent solid such as a gum (e.g. gum arabic, gum tragacanth, guar gum or xanthan gum) or components for encapsulating the composition (such as gelatin as by coacervation or a urea-formaldehyde prepolymer as by polymerization of a shell around a liquid center).

The 4,4A,5,6-tetrahydro-7-methyl-2-(3H)-naphthalenone of our invention can be also combined in proportions of from 0.1% up to 99.9% of 4,4A,5,6-tetrahydro-7-methyl-2-(3H)-naphthalenone with respect to the benzodioxanones of United States Letters Patent 4,294,266 issued on Oct. 13, 1981, the specification of which is incorporated herein by reference. Thus, the instant invention not only contemplates the organoleptic utilities of the 4,4A,5,6-tetrahydro-7-methyl-2-(3H)-naphthalenone per se having the structure:

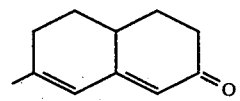

but also involves admixtures of 4,4A,5,6-tetrahydro-7-methyl-2-(3H)-naphthalenone having the structure:

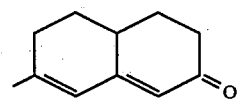

with the bicyclic compounds having the generic structure:

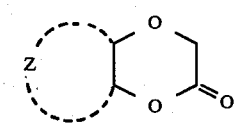

wherein Z is benzo or cyclohexano.

It will thus be apparent that the 4,4A,5,6-tetrahydro-7-methyl-2-(3H)-naphthalenone of our invention taken alone or further together with the cyclic chemical compounds defined according to the structure:

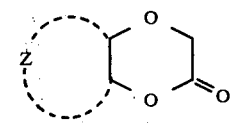

wherein Z is benzo or cyclohexano can be utilized to alter the sensory properties of consumable materials particularly organoleptic properties such as flavors and/or fragrances of a wide variety of consumable materials.

The following examples are illustrative and the invention is to be considered to be restricted thereto only as indicated in the appended claims. These examples serve to illustrate the processes for producing the 4,4A,5,6-tetrahydro-7-methyl-2-(3H)-naphthalenone useful in our invention and processes for using the 4,4A,5,6-tetrahydro-7-methyl-2-(3H)-naphthalenone of our invention for its organoleptic properties.

All parts and percentages given are by weight unless otherwise specified.

EXAMPLE I

PREPARATION OF ACETOXY CYCLOHEXADIENE DERIVATIVE MIXTURE

Reaction:

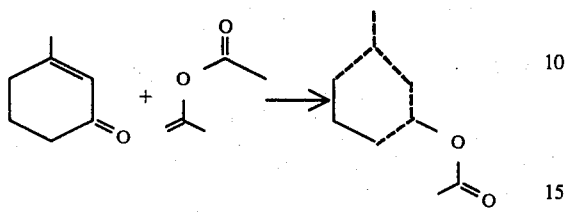

(wherein in the resulting product, in each of the molecules of the mixture, two of the dashed lines not adjacent to one another represent conjugated carbon-carbon double bonds and the other of the dashed lines represent carbon-carbon single bonds).

A twelve liter reaction flask (equipped with a 12" stone packed column and thermometer) is charged with 3,780 grams of 3-methyl-2-cyclohexenone having the structure:

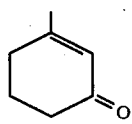

4,000 grams of isopropenyl acetate having the structure:

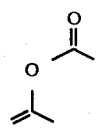

and 10 grams of para toluenesulfonic acid.

With stirring, the reaction mass is heated to reflux. Acetone (formed in the reaction) is distilled out between 40°–70° C. (vapor temperature). Completion of the reaction is monitored using GLC. 50 grams of sodium acetate is added and the product is distilled under vacuum. 5,042 grams of product is obtained having the following distillation profile:

| Vapor Temp. (°C.) | Liquid Temp. (°C.) | Pressure mm/Hg. | Weight of Fraction (grams) |
|---|---|---|---|
| 58 | 89 | 12 | 100 |
| 58–69 | 89–150 | 4 | 5042 (product) |
| 69–102 | 150–215 | 5 | 100 |

GLC, NMR and IR and mass spectral analyses yield the information that the product boiling at 58°–69° C. at 4 mm/Hg pressure consists of the compounds having the structures:

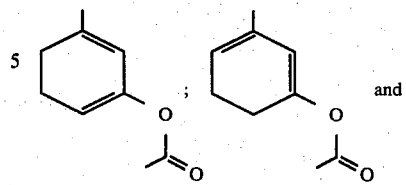

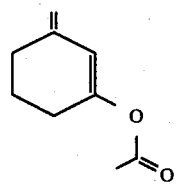

Fractions 1–10 are bulked for subsequent reaction in Example II.

FIG. 1 is the GLC profile for the crude reaction product prior to distillation (conditions: SF-96 column programmed at 100°–220° C. at 8° C. per minute). The peak indicated by the reference numeral "1" is the peak for the starting material defined according to the structure:

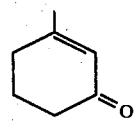

The peak indicated by reference numeral "2" is a complex peak containing a mixture of compounds defined according to the structure:

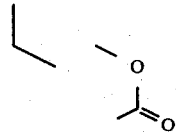

wherein in each of the molecules of the mixture, two of the dashed lines not adjacent to one another represent conjugated carbon-carbon double bonds and the other of the dashed lines represent carbon-carbon single bonds.

EXAMPLE II

PREPARATION OF METHYL-ACETYL-BICYCLO-[2.2.2]OCT-5-ENOL ACETATE INCLUDING 5-METHYL-7-ACETYL BICYCLO-[2.2.1]OCT-5-EN-1-OL ACETATE

Reaction:

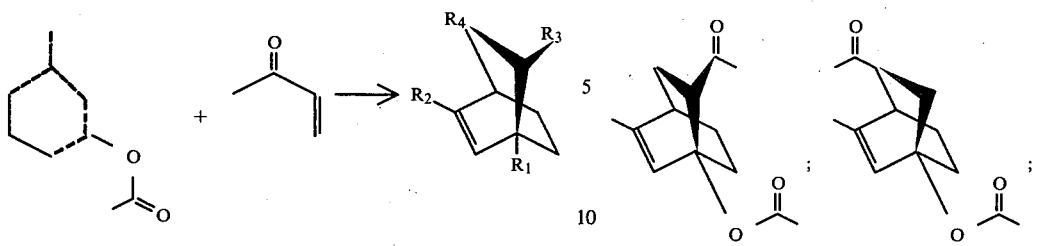

(wherein in the starting reactant mixture, in each of the molecules, two of the dashed lines not adjacent to one another represent conjugated carbon-carbon double bonds and the other of the dashed lines represent carbon-carbon single bonds; and in the reaction product mixture represented by the structure:

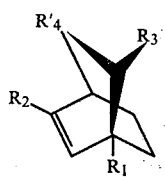

one of $R_3$ or $R_4$ represents hydrogen and the other of $R_3$ or $R_4$ represents acetyl and one of $R_1$ or $R_2$ represents methyl and the other of $R_1$ or $R_2$ represents acetoxy).

A 12 liter reaction flask (equipped with stirrer, condenser, addition funnel and thermometer) is charged with 6,243 grams of the enol ester mixture produced according to Example I defined by the structure:

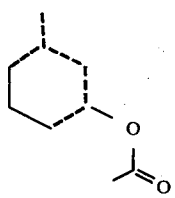

3,215 grams of methyl vinyl ketone and 10 grams of hydroquinone. The resulting mixture is heated to reflux slowly. As the reaction proceeds to completion, the pot temperature rises from 90°-170° C. Completion of the reaction is monitored using GLC. After no more product is formed, the reaction mixture is transferred to a distillation flask and distilled. 3,155 grams of the product mixture is obtained having the following distillation profile:

| Vapor Temp. (°C.) | Liquid Temp. (°C.) | Pressure mm/Hg. | Weight of Fraction (grams) |
|---|---|---|---|
| 88-92 | 131-150 | 25-5 | 1,324 (recovered starting material) |
| 122-118 | 151-232 | 5 | 3,155 (product) |

The 3,155 grams of product will be utilized in the process of Example III. The 3,155 grams of product, boiling at 118°-122° C. at 5 mm/Hg pressure contains compounds defined according to the structures:

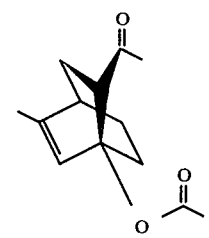

as confirmed by NMR, IR and mass spectral analyses.

FIG. 2 is the GLC profile for bulked fractions 8-13 of the foregoing distillation product.

FIG. 3 is the NMR spectrum for the compound 5-methyl-7-acetyl-bicyclo[2.2.2]oct-5-en-1-ol acetate produced according to this example, having the structure:

(CFCl$_3$ solvent; Field Strength 100 MHz).

EXAMPLE III

PREPARATION OF CRYSTALLINE 4,4A,5,6-TETRAHYDRO-7-METHYL-2-(3H)-NAPHTHALENONE

Reaction:

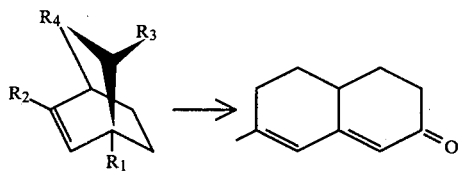

(wherein in the starting material, one of $R_3$ or $R_4$ is hydrogen and the other of $R_3$ or $R_4$ is acetyl; and one of $R_1$ or $R_2$ is methyl and the other of $R_1$ or $R_2$ is acetoxy).

A 12 liter reaction flask (equipped with stirrer, thermometer, addition funnel and large condenser) is charged with 200 grams of sodium hydroxide pellets and 6 liters of methanol. The mixture is stirred until the pellets dissolve and the mass is heated to reflux. To the refluxing solution, 650 grams of the bicyclic adduct defined according to the structures:

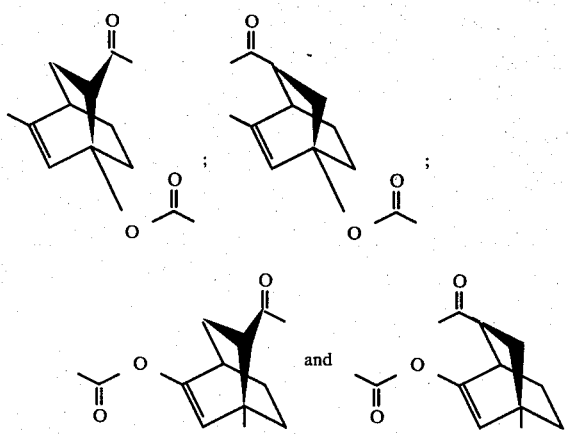

produced according to Example II is added slowly to the reaction mass. The reaction mass is refluxed for a period of 12 hours and then cooled. The reaction mass is decomposed by adding it to 6 liters of ice water and extracted with diethyl ether; washed with a saturated sodium chloride solution and dried. The solvent is stripped atmospherically and the product is distilled under vacuum at 138° C. at 2 mm/Hg pressure yielding 350 grams of crude product.

This material (the crude mixture) contains impurities. Pure (99%+) material is obtained by using column chromatography. Thus, specially treated silica gel is used as a solid support. Cyclohexane is used as a solvent. Various cuts are taken and analyzed using GLC analysis. The fractions containing 99%+ product, that is the product having the structure:

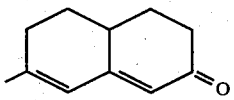

are concentrated and the product concentrate is treated with copper powder to remove the sulfur aroma. Thus, the concentrated product is admixed in hot methanol with copper powder. The resulting mixture is stirred for a period of 3 hours. The copper powder is filtered from the solution and the solution is then admixed with charcoal. The charcoal is separated from the mixture by filtration and the resultant 4,4A,5,6-tetrahydro-7-methyl-2-(3H)-naphthalenone having the structure:

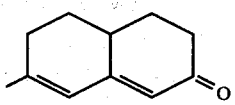

(purity greater than 99%) is precipitated from the methanol solution (by means of slow crystallization). This material has a melting point of 31°-33° C.

FIG. 4 is the GLC profile for the crude reaction product of this example (isothermal at 220° C.).

FIG. 5 is the mass spectrum for the crystals of 4,4A,5,6-tetrahydro-7-methyl-2-(3H)-naphthalenone having the structure:

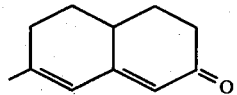

produced according to this example.

FIG. 6 is the NMR spectrum for the crystalline 4,4A,5,6-tetrahydro-7-methyl-2-(3H)-naphthalenone having the structure:

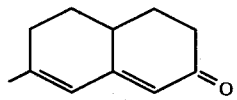

produced according to this example (CFCl₃ solvent; Field Strength, 100 MHz).

FIG. 7 is the infra-red spectrum for the crystalline 4,4A,5,6-tetrahydro-7-methyl-2-(3H)-naphthalenone having the structure:

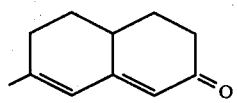

produced according to this example.

EXAMPLE IV

PREPARATION OF 4,4A,5,6-TETRAHYDRO-7-METHYL-2-(3H)-NAPHTHALENONE BY REACTING THREE MOLES OF ACETOACETIC ESTER WITH TWO MOLES OF FORMALDEHYDE FOLLOWED BY DECARBOXYLATION

Postulated possible reaction sequences:

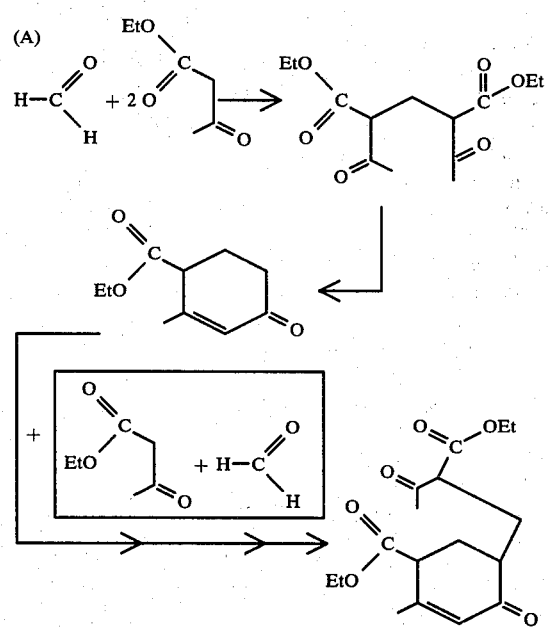

-continued

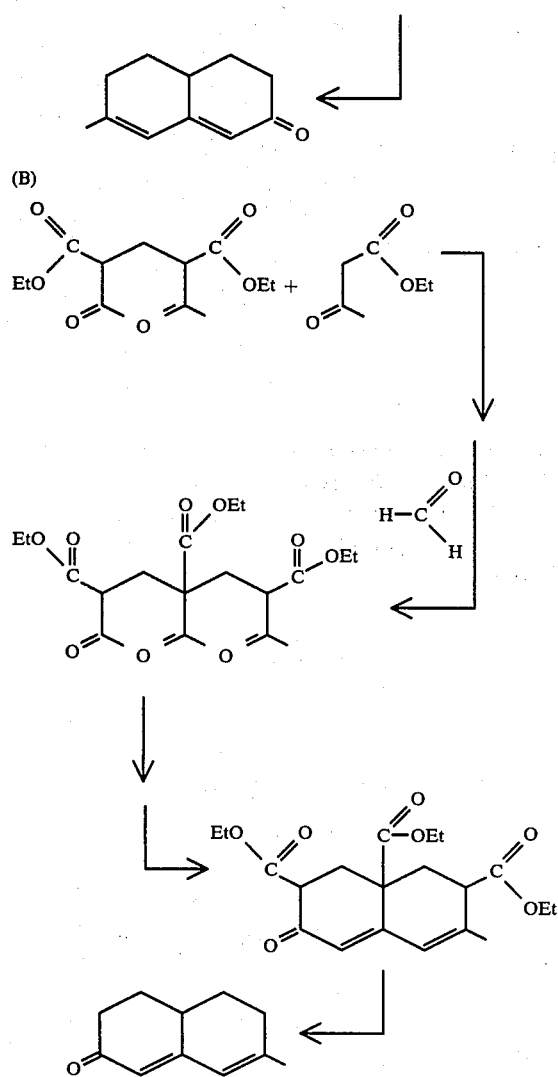

Into a 22-liter Morton reaction flask equipped with heating mantle, air stirrer, thermometer, addition funnel and reflux condenser, 3,900 grams of ethyl acetoacetate and 450 grams of paraformaldehyde are added with stirring. The resulting mixture is maintained at 23° C. and while maintaining the mixture at 23° C., over a 20 minute period, 150 ml of piperidine is added with stirring to the reaction mass.

The reaction mass is then heated to 105° C. with stirring and maintained at 95°-105° C. for a period of 1.5 hours. At the end of the 1.5 hours, the reaction mass is cooled to room temperature and 2,960 grams of 92% sulfuric acid in 9 liters of water is added to the reaction mass. The reaction mass is then refluxed at 90° C. for a period of 4 hours with stirring. At the end of the 4 hour "decarboxylation" period, the reaction mass is cooled to room temperature using an ice bath and transferred to a 50 liter separatory funnel. The reaction mass is extracted with three 2 liter portions of methylene dichloride. The organic layers are combined and washed with one 4 liter portion of water followed by one 2 liter portion of saturated sodium bicarbonate. The resulting liquid is then dried over anhydrous sodium sulfate, filtered and stripped of methylene dichloride at 80° C. at atmospheric pressure.

The reaction mass is then distilled yielding the following fractions on a 1' Goodloe column:

| Fraction Number | Vapor Temp. (°C.) | Liquid Temp. (°C.) | Pressure mm/Hg. | Reflux Ratio |
| --- | --- | --- | --- | --- |
| 1 | 40/51 | 120/127 | 3/3 | 9:1 |
| 2 | 64 | 129 | 3 | 9:1 |
| 3 | 96 | 135 | 3 | 9:1 |
| 4 | 96 | 141 | 3 | 9:1 |
| 5 | 108 | 149 | 3 | 4:1 |
| 6 | 110 | 147 | 3 | 4:1 |
| 7 | 108 | 150 | 3 | 4:1 |
| 8 | 96 | 156 | 3 | 4:1 |

Fractions 1-7 are bulked and are analyzed to be less than 80% of the compound having the structure:

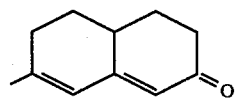

and more than 20% of the compound having the structure:

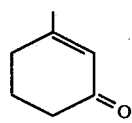

Fraction 8 is a composition of matter containing 86% of the compound having the structure:

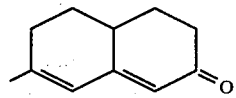

and this fraction is set aside for subsequent organoleptic utilization.

EXAMPLE V

PREPARATION OF METHYL CYCLOHEXENONE FROM TWO MOLES OF ACETOACETIC ESTER AND ONE MOLE OF FORMALDEHYDE FOLLOWED BY DECARBOXYLATION

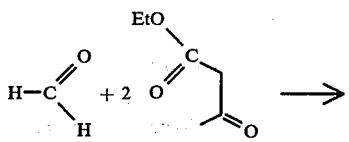

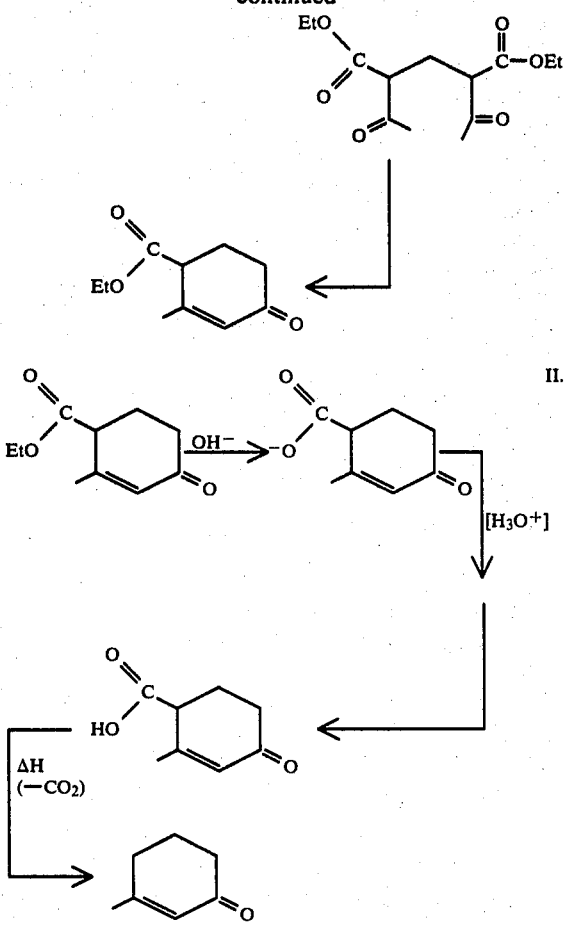

Into a 22 liter reaction flask equipped with heating mantle, air stirrer, reflux condenser, addition funnel and thermometer is placed 2,600 grams of ethyl acetoacetate and 300 grams of paraformaldehyde. Over a period of 8 minutes, 100 ml piperidine is added to the reaction mass while maintaining the temperature at 25°-26° C. The reaction mass is then heated to 90°-93° C. (reflux) and maintained at that temperature for a period of 1.25 hours. At the end of that period of time, the reaction mass is cooled and 2,960 grams of 93% sulfuric acid in 9 liters of water is added. The reaction mass is then heated to 97°-99° C. (refluxing) and maintained at that temperature for a period of 17 hours with stirring and refluxing. The reaction mass is then cooled to room temperature and steam distilled over a period of 9 hours at 94°-95° C.

The steam distillate is transferred to a 50 liter open head separatory funnel and neutralized with two liters of saturated sodium bicarbonate solution. The reaction mass is then extracted with three 2 liter portions of methylene dichloride and the organic layers are washed with one 2 liter portion of sodium chloride solution and then dried over anhydrous sodium sulfate and filtered. The methylene dichloride is then stripped off and the reaction mass is distilled yielding the following fractions:

| Fraction Number | Vapor Temp. (°C.) | Liquid Temp. (°C.) | Pressure mm/Hg. | Weight of Fraction (grams) |
|---|---|---|---|---|
| 1 | 32/62 | 52/64 | 3.0/3.0 | 45.4 |
| 2 | 57 | 60 | 2.5 | 109.3 |
| 3 | 57 | 59 | 2.5 | 105.4 |
| 4 | 58 | 60 | 2.5 | 108.2 |
| 5 | 55 | 68 | 2.5 | 98.1 |
| 6 | 60 | 100 | 2.5 | 58.0 |

Fractions 1-6 are bulked. GLC, IR, NMR and mass spectral analyses yield the information that fractions 1-6 consist essentially of the compound having the structure:

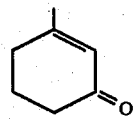

FIG. 8 is the GLC profile of the crude reaction product prior to distillation (conditions: 2' × 1/8" Carbowax column programmed at 100°-220°C. at 8°C. per minute).

The peak on the GLC profile indicated by reference numeral "3" is the peak for the methylene dichloride solvent. The peak indicated by reference numeral "4" is for the product having the structure:

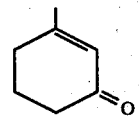

The peak indicated by reference numeral "5" is the peak for the compound, 4,4A,5,6-tetrahydro-7-methyl-2-(3H)-naphthalenone having the structure:

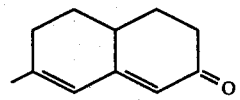

EXAMPLE VI

PERFUME COMPOSITION:

The following mixtures are prepared:

| Ingredients | Parts by Weight VI(A) | VI(B) |
|---|---|---|
| Benzyl acetate | 50 | 50 |
| Rosewood oil | 100 | 100 |
| Cedarwood oil | 150 | 150 |
| Linalyl acetate | 100 | 100 |
| Alpha-ionone | 80 | 80 |
| Ethyl cinnamate | 20 | 20 |
| Amyl cinnamic aldehyde | 50 | 50 |
| Isoeugenol | 50 | 50 |
| Methyl-3-isopropyl-6-methyl-resorcylate | 50 | 50 |
| Musk xylene | 50 | 50 |
| Styrax resin | 100 | 100 |
| Crystalline 4,4A,5,6-tetrahydro-7-methyl-2-(3H)-naphthalenone prepared according to Example III | 30 | 0 |

-continued

| Ingredients | Parts by Weight | |
|---|---|---|
| | VI(A) | VI(B) |
| Composition of matter containing 86% 4,4A,5,6-tetrahydro-7-methyl-2-(3H)-naphthalenone prepared according to Example IV, fraction 8 | 0 | 30 |

The foregoing perfume formulation is an important part of the chypre essence. The coumarin ordinarily in this formulation has been replaced by either crystalline 4,4A,5,6-tetrahydro-7-methyl-2-(3H)-naphthalenone or 86% 4,4A,5,6-tetrahydro-7-methyl-2-(3H)-naphthalenone having the structure:

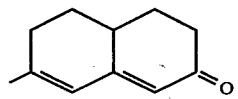

Insofar as the replacement of the coumarin with the crysalline 4,4A,5,6-tetrahydro-7-methyl-2-(3H)-naphthalenone produced according to Example III is concerned, this chypre essence has added to it a coumarin-like, tonka-like, fruity and tobacco-like aroma profile. Accordingly, the composition of Example VI(A) can be described as "Chypre with coumarin-like, tonka-like, fruity and tobacco-like undertones".

The replacement of the coumarin with the composition of matter of Example IV containing 86% 4,4A,5,6-tetrahydro-7-methyl-2-(3H)-naphthalenone gives rise to a chypre essence having added thereto coumarin-like and sweet rum aroma nuances with spicy, hay and tobacco topnotes. Accordingly, the chypre essence of Example VI(B) can be described as "chypre essence having coumarin-like and sweet rum undertones and spicy, hay and tobacco-like topnotes".

EXAMPLE VII

FOUGÈRE PERFUME FORMULATION

The following Fougère perfume formulations are prepared:

| Ingredients | Parts by Weight | |
|---|---|---|
| | VII(A) | VII(B) |
| Oakmoss absolute (50% in diethyl phthalate) | 2 | 2 |
| Bergamot oil | 15 | 15 |
| Lavender oil | 19 | 19 |
| Citronellol | 15 | 15 |
| Patchouli oil | 4 | 4 |
| Geranium oil | 5 | 5 |
| Gamma methyl ionone | 15 | 15 |
| Petitgrain oil | 2 | 2 |
| Musk ketone | 8 | 8 |
| Heliotropine | 2 | 2 |
| Clary sage oil | 2 | 2 |
| Amyl salicylate | 1 | 1 |
| 1,4-benzodioxan-2-one | 10 | 10 |
| Crystalline 4,4A,5,6-tetrahydro-7-methyl-2-(3H)-naphthalenone produced according to Example III | 5 | 0 |
| 86% 4,4A,5,6-tetrahydro-7-methyl-2-(3H)-naphthalenone produced according to Example IV, fraction 8 | 0 | 5 |

The 1,4-benzodioxan-2-one taken in combination with the 4,4A,5,6-tetrahydro-7-methyl-2-(3H)-naphthalenone of our invention gives surprising strength to this Fougère formulation and, in addition, acts as a fixative therefor. Addition of the mixture also creates a natural and diffusive coumarin-like, tonka-like, fruity and tobacco-like aroma in the case of Example VII(A). Accordingly, the fragrance of Example VII(A) can be termed as "Fougère with a natural and diffusive coumarin-like, tonka-like, fruity and tobacco-like undertone". The composition containing 86% 4,4A,5,6-tetrahydro-7-methyl-2-(3H)-naphthalenone prepared according to Example IV (fraction 8) adds to this Fougère formulation a sweet, rum and coumarin-like aroma with spicy, hay and tobacco-like topnotes. Accordingly, the fragrance formulation of Example VII(B) can be described as "Fougère with a coumarin and sweet rum undertone and spicy, hay-like and tobacco-like topnotes".

EXAMPLE VIII

PERFUMED LIQUID DETERGENT

Concentrated liquid detergents with aroma nuances as set forth in Table I, infra, are prepared containing 0.10%, 0.15%, and 0.20% of one of the substances as set forth in Table I, infra. They are prepared by adding and homogeneously mixing the appropriate quantity of substance set forth in Table I, infra, in the liquid detergent. The detergents all possess aromas as set forth in Table I, infra:

TABLE I

| Perfume Substance | Aroma Profile |
|---|---|
| Crystalline 4,4A,5,6-tetrahydro-7-methyl-2-(3H)-naphthalenone prepared according to Example III | A natural and diffusive coumarin-like and tonka-like, fruity and tobacco-like aroma. |
| 86% 4,4A,5,6-tetrahydro-7-methyl-2-(3H)-naphthalenone prepared according to Example IV, distillation fraction 8 | A coumarin-like, sweet rum-like aroma with spicy, hay and tobacco-like topnotes. |
| Perfume composition of Example VI(A) | Chypre with coumarin-like, tonka-like, fruity and tobacco-like undertones. |
| Perfume composition of Example VI(B) | Chypre essence having coumarin-like and sweet rum undertones and spicy, hay and tobacco-like topnotes. |
| Perfume composition of Example VII(A) | Fougère with a natural and diffusive coumarin-like, tonka-like, fruity and tobacco-like undertone. |
| Perfume composition of Example VII(B) | Fougère with a coumarin and sweet rum undertone and spicy, hay-like and tobacco-like topnotes. |

EXAMPLE IX

PREPARATION OF COLOGNES AND HANDKERCHIEF PERFUMES

Each of the perfumery substances as set forth in Table I of Example VIII is incorporated individually into colognes at concentrations of 1.5%, 2.0%, 2.5%, 3.0%, 3.5% and 4.0% in 80%, 85%, and 90% aqueous ethanol; and into handkerchief perfumes at concentrations of 10%, 15%, 20% and 25% (in 80%, 85%, 90% and 95% aqueous ethanol compositions). In each of the compositions tested, distinct and definitive aromas as set forth in Table I of Example VIII are imparted to the colognes and to the handkerchief perfumes.

EXAMPLE X

PREPARATION OF A SOAP COMPOSITION

One hundred grams of soap chips (IVORY ® manufactured by the Procter & Gamble Company of Cincinnati, Ohio) are mixed with one gram of each of the perfumery substances, on an individual basis, of Table I of Example VIII. The resulting mixture is melted and maintained at 8 atmospheres pressure and 150° C. for a period of 5 hours. The soap is then placed in molds and the thus formed liquid soap is cooled to room temperature. Each of the soap cakes is then aged for a period of one week under 8 atmospheres nitrogen pressure.

Each of the soap cakes manifests a pleasant aroma as set forth in Table I of Example VIII, supra.

EXAMPLE XI

PREPARATION OF A SOLID DETERGENT COMPOSITION

A detergent is prepared from the following ingredients according to Example I of Canadian Pat. No. 1,007,948, the specification of which is incorporated by reference herein.

| Ingredients | Parts by Weight |
|---|---|
| Neodol 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

Each of the detergents is a "phosphate-free" detergent. A total of 100 grams of this detergent is admixed with 0.15 grams of each of the perfumery substances of Table I of Example VIII (on an individual basis). Each of the detergent samples has excellent diffusive aromas as set forth in Table I of Example VIII.

EXAMPLE XII

PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976, the specification of which is incorporated by reference herein) with aromas as set forth in Table I of Example VIII are prepared containing 0.50% of each of the perfumery formulations of Table I of Example VIII. They are prepared by adding and homogeneously mixing the appropriate quantity of perfume formulation in the liquid detergent. The detergents all possess aromas as set forth in Table I of Example VIII.

EXAMPLE XIII

FABRIC SOFTENER ARTICLE

Utilizing the procedure of Example 1 of column 15 of U.S. Pat. No. 3,632,396 (the disclosure of which is incorporated by reference herein) a non-woven cloth substrate useful as a drier-added fabric softening article of manufacture is prepared wherein the substrate, the substrate coating and the outer coating and the perfuming material are as follows:
1. a water dissolvable paper ("Dissolvo Paper") as the base
2. Adogen 448 (m.p. about 140° F.) as the substrate coating, and
3. an outer coating having the following formulation (m.p. about 150° F.):

$$\begin{bmatrix} 57\% \text{ } C_{20\text{-}22} \text{ HAPS} \\ 22\% \text{ isopropyl alcohol} \\ 20\% \text{ antistatic agent} \\ 1\% \text{ of each of the perfumery substances on} \\ \text{an individual basis as set forth in} \\ \text{Table I of Example VIII, supra.} \end{bmatrix}$$

A fabric softening composition prepared as set forth above having aroma characteristics as set forth in Table I of Example VIII consists of a substrate having a weight of about 5 grams per 100 square inches; a substrate coating having a weight of about 1.85 grams per 100 square inches of substrate and an outer coating having a weight of about 1.4 grams per 100 square inches of substrate, thereby providing a total aromatized substrate and outer coating weight ratio of about 1:1 by weight of the substrate. The aromas as set forth in Table I of Example VIII are imparted in a pleasant manner to the head space in the drier on operation thereof using the said drier-added fabric softening non-woven fabric.

EXAMPLE XIV

PERFUMED POLYMER

Scented polyethylene pellets having aromas as set forth in Table I of Example VIII are prepared according to the procedure of Example III of U.S. Pat. No. 3,505,432 issued on Apr. 7, 1970, the disclosure for which is incorporated by reference herein. Thus, 75 pounds of polyethylene having a melting point of about 220° F. are heated to about 230° F. in a container as illustrated in FIGS. 1 and 2 of U.S. Pat. No. 3,505,432. Twenty-five pounds of one of the perfume materials of Table I of Example VIII are then quickly added to the liquid polyethylene and the lid in the apparatus is put in place and the agitating means are actuated. The temperature is maintained at about 225° F. and the mixing is continued for about 5–15 minutes. The valve is then opened in order to allow flow of the molten polyethylene enriched with the scented material to exit through orifices in the apparatus. The liquid falling through the orifices solidifies almost instantaneously upon impact with the moving cooled conveyor part of the apparatus. The solid polyethylene beads or pellets having a pronounced scent as set forth in Table I of Example VIII are thus formed. Analysis demonstrates that the pellets contain almost about 25% of the particular perfume substance set forth in Table I of Example VIII so that almost no losses of the scenting substance occur. These pellets are called master pellets. Fifty pounds of the said master pellets are then added to 1,000 pounds of unscented polyethylene powder and the mass is heated to the liquid state. The liquid is molded into thin sheets or films. The sheets or films have a pronounced aroma as set forth in Table I of Example VIII. When polypropylene replaces the polyethylene, a substantially identical result occurs.

EXAMPLE XV

VANILLA FLAVOR

The following formulation is prepared:

| | |
|---|---|
| Vanillin | 10.00 grams |
| Ethyl vanillin | 3.00 grams |
| Benzodihydropyrone | 3.00 grams |
| Heliotropin | 1.00 gram |
| Propenyl guiacol | 0.50 gram |
| Gamma nonyl lactone | 0.25 gram |
| Gamma undecalactone | 0.25 gram |
| Delta dodecalactone | 0.25 gram |
| 4,4A,5,6-tetrahydro-7-methyl-2-(3H)-naphthalenone having the structure: | 0.10 gram |

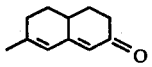

produced according to Example III

The 4,4A,5,6-tetrahydro-7-methyl-2-(3H)-naphthalenone having the structure:

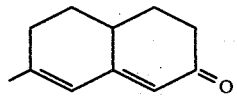

enhances the foregoing vanilla formulation (a) making it more natural-like; (b) imparting a courmarin-like, coconut-like aroma and a coumarin-like, coconut-like, almond-like, macaroon-like taste. The formulation is three times as powerful as the formulation without this compound added thereto. In addition, the formulation is rendered much more outstanding in a standard Creme-de-Kahlua formulation causing the Creme-de-Kahlua formulation to be more natural-like and preferred by a bench panel of five members, unanimously. The resulting formulation containing the compound having the structure:

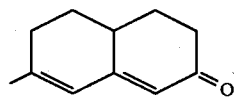

is added to the following liqueur formulation:

| Ingredients | Parts by Weight |
|---|---|
| Clove essential oil | 780 |
| Lemon essential oil | 400 |
| Orange essential oil | 300 |
| Cinnamon essential oil | 250 |
| Mace essential oil | 180 |
| Vanillin formulation (as set forth above) | 150 |
| Neroli essential oil | 10 |
| Citronellol | 2 |
| Rose absolute | 1 |
| Food grade ethanol | 927 |

The resulting liqueur is added to the following mixture in order to produce a consumable commercial material:

| Ingredients | Parts by Weight |
|---|---|
| 96% food grade ethanol | 301 kg |
| Sugar | 40 kg |
| Distilled water | 46.8 liters |

-continued

| Ingredients | Parts by Weight |
|---|---|
| Flavor (as set forth above) (0.5% in food grade ethanol) | 0.5 kg |

The resulting liqueur has an interesting, bitter almond taste and aroma with coconut nuances making it useful as such or as a "Bagne" for a sauce used for soaking pound cakes such as "Rum BaBa".

EXAMPLE XVI

The vanilla flavor of Example XV is placed into an ice cream mix at a rate of 0.10%. The resulting previously-unflavored ice cream has an excellent vanilla flavor.

EXAMPLE XVII

BASIC WALNUT FLAVOR FORMULATION

The following basic walnut formulation is prepared:

| Ingredients | Parts by Weight |
|---|---|
| Cyclotene | 4.0 |
| Vanillin | 1.0 |
| Butylisovalerate | 2.0 |
| Benzaldehyde | 6.0 |
| 2,3-diethyl pyrazine (10% in food grade ethanol) | 2.0 |
| Ethyl-2-methyl valerate | 2.0 |
| Gamma butyrolactone | 20.0 |
| Gamma hexenolactone | 10.0 |
| 2,4-decadienal (0.1% in food grade ethyl alcohol) | 0.5 |
| 2,4-heptadienal (0.1% in food grade ethyl alcohol) | 0.5 |
| Butylidene phthalide | 2.0 |
| Propylene glycol USP | 95.0 |

The formulation is divided into two parts. To one of the parts 0.8% by weight of the 86% composition of 4,4A,5,6-tetra-7-methyl-2-(3H)-naphthalenone having the structure:

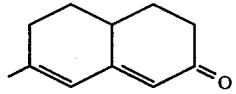

produced according to Example IV, distillation fraction 8, is added. To the second part of the basic walnut formulation, nothing else is added. Both formulations with and without the additional material are compared at the rate of 100 ppm in water by a bench panel. All members of the bench panel prefer the walnut flavor with the addition of the compound prepared according to Example IV having the structure:

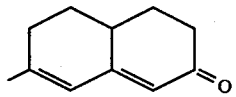

as a result of additional characteristic walnut notes and bitter mouth feel effects being present.

EXAMPLE XVIII

A. Powder Flavor Composition

Twenty grams of the flavor composition of Example XVII is emulsified in a solution containing 300 grams gum acacia and 700 grams of water. The emulsion is spray dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredient | Parts by Weight |
| --- | --- |
| Liquid walnut flavor composition of Example XVII | 20 |
| Propylene glycol | 9 |
| Cab-O-Sil ® M-5 (brand of silica produced by the Cabot Corp. of 125 High St., Boston, Mass. 02110 Physical Properties: Surface area: 200 m²/gm Nominal particle size: 0.012 microns Density: 2.3 lbs/cu. ft.) | 5 |

The Cab-O-Sil® is dispersed in the liquid walnut flavor composition of Example XVII with vigorous stirring thereby resulting in a viscous liquid. Seventy-one parts by weight of the powder flavor composition of Part A, supra, is then blended into said viscous liquid with stirring at 25° C. for a period of 30 minutes resulting in a dry, free-flowing sustained release flavor powder.

EXAMPLE XIX

Ten parts by weight of 50 Bloom pigskin gelatin is added to ninety parts by weight of water at a temperature of 150° F. The mixture is agitated until the gelatin is completely dissolved and the solution is cooled to 120° F. Twenty parts by weight of the liquid flavor composition of Example XVII is added to the solution which is then homogenized to form an emulsion having a particle size typically in the range of 2-5 microns. The material is kept at 120° F. under which conditions the gelatin will not gel.

Coacervation is induced by adding slowly and uniformly, forty parts by weight of a 20% aqueous solution of sodium sulphate. During coacervation of gelatin, molecules are deposited uniformly about each oil droplet as a nucleus.

Gelation is effected by pouring the heated coacervate mixture into 1,000 parts by weight of a 7% aqueous solution of sodium sulphate at 65° F. The resulting gelled coacervate may be filtered and washed with water at temperatures below the melting point of gelation, to remove the salt.

Hardening of the filter cake, in this example, is effected by washing with 200 parts by weight of 37% solution of formaldehyde in water. The cake is then washed to remove the residual formaldehyde.

EXAMPLE XX

CHEWING GUM

One hundred parts by weight of chicle are mixed with four parts by weight of the flavor prepared in accordance with Example XVIII, Part B. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips one inch in width and 0.1 inchs in thickness. The strips are cut into lengths of three inches each. On chewing, the chewing gum has a pleasant, long-lasting sweet, fruity, walnut flavor.

EXAMPLE XXI

CHEWING GUM

One hundred parts by weight of chicle are mixed with eighteen parts by weight of the flavor prepared in accordance with Example XVIII. Three hundred parts of sucrose and one hundred parts of corn syrup are then added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting sweet, fruity, walnut flavor.

EXAMPLE XXII

TOOTHPASTE FORMULATION

The following separate groups of ingredients are prepared:

| Parts by Weight | Ingredients |
| --- | --- |
| Group "A" | |
| 30.200 | Glycerine |
| 15.325 | Distilled water |
| 0.100 | Sodium benzoate |
| 0.125 | Saccharin sodium |
| 0.400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example XVIII, Part B |
| 100.000 (total) | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour.

The completed paste is then transferred to a three roller mill and then homogenized, and finally tubed.

The resulting toothpaste, when used in a normal tooth-brushing procedure, yields a pleasant, sweet, walnut flavor of constant strong intensity throughout said procedure (1-1.5 minutes).

EXAMPLE XXIII

CHEWABLE VITAMIN TABLETS

The flavor material produced according to the process of Example XVIII, Part B, is added to a chewable vitamin tablet formulation at a rate of 10 gm/kg which chewable vitamin tablet formulation is prepared as follows:

In a Hobart Mixer, the following materials are blended to homogeneity:

| Ingredients | Gms/1000 Tablets |
|---|---|
| Vitamin C (ascorbic acid as ascorbic acid-sodium ascorbate mixture 1:1) | 70.000 |
| Vitamin B$_1$ (thiamine mononitrate) as Rocoat ® thiamine mononitrate 33⅓% (Hoffman LaRoche) | 4.000 |
| Vitamin B$_2$ (riboflavin) as Rocoat ® riboflavin 33⅓% | 5.000 |
| Vitamin B$_6$ (pyridoxine hydrochloride) as Rocoat ® pyridoxine hydrochloride 33⅓% | 4.000 |
| Niacinamide as Rocoat ® niacinamide 33⅓% | 33.000 |
| Calcium pantothenate | 11.500 |
| Vitamin B$_{12}$ (cyanocobalamin) as Merck 0.1% in gelatin | 3.500 |
| Vitamin E (dl-alpha tocopheryl acetate) as dry Vitamin E acetate 33⅓% Roche | 6.600 |
| d-Biotin | 0.044 |
| Certified lake color | 5.000 |
| Flavor of Example XVIII, Part B | as indicated above |
| Sweetener sodium saccharin | 1.000 |
| Magnesium stearate lubricant | 10.000 |
| Mannitol q.s. to make | 500.000 |

Preliminary tablets are prepared by slugging with flat-faced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong, sweet, walnut flavor for a period of 12 minutes.

EXAMPLE XXIV

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn syrup | 60.0 |
| Licorice | 10.0 |
| Glycerine | 20.0 |
| Fig juice | 4.6 |
| Prune juice | 5.0 |
| Flavor material of Example XVIII, Part B | 0.4 |

The resultant product is redired to a moisture content of 20%. On chewing, this tobacco has an excellent substantially consistent, long-lasting, sweet, green, walnut (20 mnutes) nuance in conjunction with the main fruity tobacco note.

EXAMPLE XXV

SMOKING TOBACCO FORMULATION

A tobacco mixture is produced by admixing the following ingredients:

| Ingredients | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

Cigarettes are prepared from this tobacco.
The following flavor formulation is prepared:

| Ingredients | Parts by Weight |
|---|---|
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above-stated tobacco formulation is applied at the rate of 0.1% to all of the cigarettes produced using the above tobacco formulation. One-third of the cigarettes are then treated with 500 or 1,000 ppm of 4,4A,5,6-tetrahydro-7-methyl-2-(3H)-naphthalenone produced according to Example III having the structure:

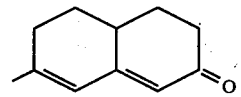

One-third of the cigarettes are also treated with 500 or 1,000 ppm of the 86% mixture of 4,4A,5,6-tetrahydro-7-methyl-2-(3H)-naphthalenone having the structure:

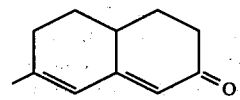

prepared according to Example IV, distillation fraction 8.

Control cigarettes not containing 4,4A,5,6-tetrahydro-7-methyl-2-(3H)-naphthalenone produced according to either of Example III or IV and the experimental cigarettes which contain the 4,4A,5,6-tetrahydro-7-methyl-2-(3H)-naphthalenone produced according to Example III and Example IV are then evaluated by paired comparison and the results are as follows:

The experimental cigarettes containing the composition prepared according to Example III have sweet, lactonic, coconut-like, creamy, coumarin-like, waxy, and heliotropin-like aroma nuances prior to smoking; and sweet, smoothing rich, coumarin-like aroma and taste nuances on smoking in the main stream and the side stream.

The experimental cigarettes containing the composition of matter of Example IV, distillation fraction 8, (86% of 4,4A,5,6-tetrahydro-7-methyl-2-(3H)-naphthalenone having the structure:

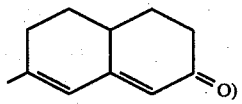

have, prior to smoking, a sweet, fruity, juicy, rum-like, sugary, woody and coconut-like aroma and on smoking, a sweet, creamy, coconut-like, rum-like, caramellic-like aroma in the main stream and the side stream.

In general, the products of Examples III and IV enhanced the tobacco-like taste and aroma of blended cigarettes imparting to them, in general, rum-like, sweet and vanilla-like tobacco notes.

EXAMPLE XXVI

FLAVORED FOODSTUFF 2.25 ounces of a coconut macaroon mix distributed by Drake Bakeries Division of Borden, Inc. of Columbus, Ohio 43215 is intimately admixed at the level of 10 ppm with (i) the 4,4A,5,6-tetrahydro-7-methyl-2-(3H)-naphthalenone produced according to Example III or (ii) the 86% 4,4A,5,6-tetrahydro-7-methyl-2-(3H)-naphthalenone composition produced according to Example IV (distillation fraction 8).

The coconut macaroon composition contains corn syrup, coconut, sugar and egg whites.

The coconut macaroon composition is then baked at 325° F. at atmospheric pressure for a period of 20 minutes. The resultant coconut macaroon cookies have an excellent "natural coconut" coumarin-like note not present in the cookies without the compositions of Examples III or IV.

What is claimed is:

1. A composition of matter comprising 4,4A,5,6-tetrahydro-7-methyl-2-(3H)-naphthalenone having the structure:

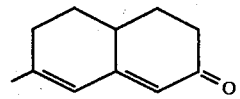

and intimately admixed therewith at least one bicyclic compound defined according to the generic structure:

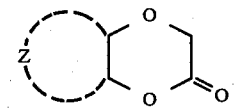

wherein Z is benzo or cyclohexano, the proportion of said naphthalenone in said mixture being from 0.1% up to 99.9% by weight of said mixture.

2. A process for augmenting or enhancing the aroma or taste of a consumable material selected from the group consisting of foodstuffs and perfume compositions comprising the step of adding to a foodstuff or a perfume composition an aroma or taste augmenting or enhancing quantity of a mixture defined according to claim 1, said naphthalenone being present in foodstuffs in an amount of 0.1 parts per million up to about 20 parts per million and said naphthalenone being present in perfume compositions in an amount of 0.02% to 10%.

* * * * *